(12) United States Patent
Natori et al.

(10) Patent No.: US 8,637,837 B2
(45) Date of Patent: Jan. 28, 2014

(54) CHARGED PARTICLE IRRADIATION SYSTEM AND METHOD FOR CONTROLLING THE SAME

(75) Inventors: Takayoshi Natori, Kasumigaura (JP); Kunio Moriyama, Hitachi (JP); Koji Matsuda, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 132 days.

(21) Appl. No.: 12/892,225

(22) Filed: Sep. 28, 2010

(65) Prior Publication Data

US 2011/0073778 A1    Mar. 31, 2011

(30) Foreign Application Priority Data

Sep. 30, 2009    (JP) ................. 2009-226878

(51) Int. Cl.
*G21G 5/00* (2006.01)
(52) U.S. Cl.
USPC .......................................... 250/492.1; 378/65
(58) Field of Classification Search
USPC ............. 250/306–307, 492.1, 492.3
See application file for complete search history.

(56) References Cited

U.S. PATENT DOCUMENTS

| 7,102,144 | B2 |  | 9/2006 | Matsuda et al. |  |
|---|---|---|---|---|---|
| 7,301,162 | B2 | * | 11/2007 | Matsuda et al. | ........... 250/505.1 |
| 7,598,504 | B2 | * | 10/2009 | Kimura et al. | ............. 250/492.2 |
| 2004/0227104 | A1 | * | 11/2004 | Matsuda et al. | ........... 250/492.1 |
| 2006/0102856 | A1 | * | 5/2006 | Matsuda et al. | ........... 250/492.1 |
| 2008/0067423 | A1 | * | 3/2008 | Kimura et al. | ............. 250/492.1 |
| 2009/0154650 | A1 |  | 6/2009 | Tanabe |  |
| 2009/0289194 | A1 | * | 11/2009 | Saito | ........................ 250/396 R |

FOREIGN PATENT DOCUMENTS

| EP | 1 477 206 A1 | 11/2004 |
|---|---|---|
| JP | 3681744 B2 | 5/2005 |
| JP | 2008-237687 A | 10/2008 |
| JP | 2008237687 A  * | 10/2008 |
| JP | 2009-66106 A | 4/2009 |
| JP | 2009-142444 A | 7/2009 |

* cited by examiner

*Primary Examiner* — David A Vanore
*Assistant Examiner* — Wyatt Stoffa
(74) *Attorney, Agent, or Firm* — Mattingly & Malur, PC

(57) ABSTRACT

A beam extraction process (interruption and restart) is appropriately performed when a failure occurs during irradiation of a spot group. A charged particle irradiation system includes a synchrotron 12 and a scanning irradiation unit 15 that scans an ion beam extracted from the synchrotron over a subject. The extraction of the ion beam from the synchrotron is stopped on the basis of a beam extraction stop command. Scanning magnets 5A and 5B are controlled to change a point (spot) to be irradiated with the ion beam, while the extraction of the ion beam is stopped. The extraction of the ion beam from the synchrotron is restarted after the change of the spot to be irradiated. When a relatively minor failure in which continuous irradiation would be possible occurs during irradiation of a certain spot with the beam, the extraction of the beam is not immediately stopped.

10 Claims, 14 Drawing Sheets

FIG.5

| SLICE (LAYER) | POSITION IN X DIRECTION | POSITION IN Y DIRECTION | TARGET DOSE | SLICE CHANGING FLAG | IRRADIATION INTERRUPT -ENABLED FLAG |
|---|---|---|---|---|---|
| 1 | −10 | −4.5 | 70 | 0 | 0 |
| 1 | −9 | −4.5 | 140 | 0 | 0 |
| ⋮ | ⋮ | ⋮ | ⋮ | ⋮ | ⋮ |
| 1 | 9 | −4.5 | 1400 | 0 | |
| 1 | 10 | −4.5 | 1470 | 0 | 1 |
| 1 | 10 | −3.5 | 1540 | 0 | 0 |
| 1 | 9 | −3.5 | 1610 | 0 | 0 |
| ⋮ | ⋮ | ⋮ | ⋮ | ⋮ | ⋮ |
| 1 | −9 | −3.5 | 2870 | 0 | 0 |
| 1 | −10 | −3.5 | 2940 | 0 | 0 |
| 1 | −10 | −2.5 | 3010 | 0 | 0 |
| ⋮ | ⋮ | ⋮ | ⋮ | ⋮ | ⋮ |
| 1 | −10 | 4.5 | 14700 | 1 | 1 |
| 2 | −10 | −4.5 | 14725 | 0 | 0 |
| 2 | 9 | −4.5 | 14750 | 0 | 0 |
| ⋮ | ⋮ | ⋮ | ⋮ | ⋮ | ⋮ |
| 2 | 9 | −4.5 | 15200 | 0 | 0 |
| 2 | 10 | −4.5 | 15225 | 0 | 1 |
| 2 | 10 | −3.5 | 15250 | 0 | 0 |
| 2 | 9 | −3.5 | 15275 | 0 | 0 |
| ⋮ | ⋮ | ⋮ | ⋮ | ⋮ | ⋮ |
| 2 | −9 | −3.5 | 15725 | 0 | 0 |
| 2 | −10 | −3.5 | 15750 | 0 | 0 |
| 2 | −10 | −2.5 | 15775 | 0 | 0 |
| ⋮ | ⋮ | ⋮ | ⋮ | ⋮ | ⋮ |
| 2 | −10 | 4.5 | 19950 | 1 | 1 |
| 3 | −10 | −4.5 | 19968 | 0 | 0 |
| 3 | −9 | −4.5 | 19986 | 0 | 0 |
| ⋮ | ⋮ | ⋮ | ⋮ | ⋮ | ⋮ |
| 3 | 9 | −4.5 | 20310 | 0 | 0 |
| 3 | 10 | −4.5 | 20328 | 0 | 1 |
| 3 | 10 | −3.5 | 20346 | 0 | 0 |
| 3 | 9 | −3.5 | 20364 | 0 | 0 |
| ⋮ | ⋮ | ⋮ | ⋮ | ⋮ | ⋮ |
| ⋮ | ⋮ | ⋮ | ⋮ | ⋮ | ⋮ |

CHARGED PARTICLE IRRADIATION SYSTEM AND METHOD FOR CONTROLLING THE SAME

BACKGROUND OF THE INVENTION

1. Field of the Invention

The present invention relates to a charged particle irradiation system and a method for controlling the charged particle irradiation system. The invention more particularly relates to a charged particle irradiation system that irradiates a patient with a charged particle beam such as protons or carbon ions and treats the patient, and a method for controlling the charged particle irradiation system.

2. Description of the Related Art

A treatment method is known for irradiating an affected part (cancer or the like) of a patient with a charged particle beam (ion beam) such as protons or carbon ions. A charged particle irradiation system used for such a treatment includes an ion beam generator, a beam transport line and an irradiation unit.

Examples of irradiation methods adopted by the irradiation unit include a passive irradiation method in which a beam is spread by means of a scatterer and is then extracted in conformity with the shape of an affected part; and a scanning irradiation method in which a fine beam is scanned across an affected part.

In a charged particle irradiation system using the scanning method, a charged particle beam is accelerated by an accelerator included in an ion beam generator and reaches an irradiation unit through a beam transport line. Scanning magnets provided in the irradiation unit deflect the charged particle beam for scanning. After that, the irradiation unit irradiates the affected part of the patient with the charged particle beam.

In this method, the extraction of the charged particle beam is stopped according to the accumulated dose of beams with which a subject is irradiated. With the extraction of the charged particle beam stopped, associated energy and the scanning magnets are controlled so that the position of a point (spot) to be irradiated with the charged particle beam is changed. After the position of the spot is completely changed, the irradiation unit restarts outputting the charged particle beam. Then, the irradiation unit irradiates the subject (affected part) while the position of the point to be irradiated is changed (refer to Japanese Patent No. 3681744, for example).

To prevent healthy cells from being exposed to the charged particle beam and perform an appropriate irradiation treatment without excessively or deficiently irradiating with the charged particle beam, a charged particle irradiation system described in Japanese Patent No. 3681744 has an irradiation unit that includes a beam position monitor and a dose monitor. The beam position monitor and the dose monitor are located on a downstream side of magnets and in front of a patient subject to be irradiated, and serve as irradiation dose detectors for measuring the dose of the charged particle beam with which the subject is irradiated.

In general, the beam position monitor is operated in such a manner that charges ionized by passing the beam are accumulated in a capacitor and a voltage induced in the capacitor after the spot irradiation is read out. The capacitance of the capacitor is determined so that the capacitor can store charges ionized when a spot is to be irradiated with the largest dose of the beam among expected doses. In the aforementioned method, the smaller the capacitance of the capacitor, the higher the resolution; and the larger the capacitance of the capacitor, the lower the resolution.

The charged particle irradiation system using the scanning method is configured as follows. The charged particle irradiation system divides a subject to be irradiated into some spots or points to be irradiated. The number of times of fractionated irradiation and an irradiation dose for each time of the irradiation are preset. The irradiation is performed on a single spot multiple times. Thus, a single irradiation dose (irradiation time) required for irradiation of each spot is reduced, and a variation in the irradiation dose is suppressed. The actual irradiation doses can be more reliably detected and evaluated (evaluation of the dose distribution and the like).

A control system for the charged particle irradiation system has an interlock. The interlock monitors failures that occur in the system and the constituent devices. In addition, the interlock monitors the state of the beam that is present in the accelerator. Even when a spot is being irradiated, if a failure occurs in the system or any of the constituent devices, the interlock is adapted to stop or interrupt the irradiation based on the type or level of the cause of the failure. In addition, the irradiation can manually be interrupted or stopped (or by pressing a button or the like).

Respiratory gating may be applied to the charged particle irradiation system in some cases. The respiratory gating is to interrupt and restart irradiation in synchronization with breathing of a patient. Specifically, the respiratory gating is such that beam irradiation starts and stops in response to a respiratory gating signal that is synchronized with breathing of the patient (when the signal is turned on, the beam irradiation is performed).

When a failure occurs or the respiratory gating signal is turned off during irradiation of a certain spot and its irradiation is interrupted or stopped, the irradiation dose (irradiation time) for the spot in question may be smaller (shorter) than a preset dose (preset time) depending on the timing of the occurrence of the failure. In consideration of characteristics of the aforementioned position monitor and effects of background noise and the like, it is difficult to accurately detect the position of the irradiated spot. As a result, it is difficult for an irradiation position detecting unit that includes the dose monitor to appropriately detect the actual dose of the beam with which the spot is irradiated. In addition, it is also difficult to appropriately evaluate the dose (evaluation of a dose distribution or the like). In this case, a single spot is irradiated multiple times with a smaller dose of the beam than the preset dose. Also, it is more difficult to appropriately detect and evaluate the actual irradiation dose of the beam with which the spot is irradiated. This will obstruct the system's efficient operation.

To avoid this problem, a charged particle therapy system described in JP-2008-237687-A does not immediately stop extraction of a charged particle beam (irradiation with the charged particle beam) when a relatively minor failure (in which continuous irradiation would be possible) occurs during the irradiation of a certain spot. More specifically, this charged particle therapy system is adapted to stop the extraction of the charged particle beam (irradiation with the charged particle beam) after the dose of the beam with which the spot is irradiated reaches a target dose.

Thus, even when a failure occurs during the irradiation of the certain spot, the irradiation is continuously performed on the spot. Therefore, it is unnecessary to irradiate a single spot multiple times separately (or it is unnecessary to interrupt and restart the irradiation), and it is possible to reliably irradiate the spot at one time. It is also possible to detect and evaluate (evaluation of the dose distribution and the like) the actual irradiation dose at a level similar to that at which normal spot irradiation is performed, while the actual irradiation dose (irradiation time) is not smaller (shorter) than a preset dose (preset irradiation time).

SUMMARY OF THE INVENTION

The conventional technique described in JP-2008-237687-A has the following problem. In general, an irradiation dose distribution is used to evaluate a group of spots rather than a single spot. It may be advantageous in some cases that spots are managed as a spot group. When a failure occurs or the respiratory gating signal is turned off during irradiation of a group of spots that are to be irradiated with beams having the same energy, and the irradiation is interrupted or stopped before completion of the irradiation, the positions of spots irradiated before the interruption of the irradiation do not necessarily match the positions of spots irradiated after the interruption of the irradiation (or the dose distribution is accordingly divided) depending on the timing of the occurrence of the failure. Since, in such a case, unexpected gaps between spots or unexpected overlapped spots are generated, a distribution of the doses of beams with which the spot group is irradiated may not be obtained as desired.

An object of the present invention is to provide a charged particle irradiation system that appropriately performs a beam extraction process (interruption and restart) when a failure occurs during irradiation of a group of spots and that safely and efficiently performs irradiation with high accuracy, and a method for controlling the charged particle irradiation system.

To accomplish the aforementioned object, when a relatively minor failure (in which continuous irradiation would be possible) occurs during irradiation of a certain spot or a respiratory gating signal is turned off, extraction of a charged particle beam (irradiation with the charged particle beam) is interrupted or stopped after completion of irradiation of all spots that belong to a spot group that includes the certain spot without immediately stopping the extraction of the charged particle beam.

Thus, even when a failure occurs during the irradiation of the certain spot or the respiratory gating signal is turned off, the irradiation is continuously performed on the spot group that includes the certain spot. Therefore, the irradiation can be reliably performed on the group of spots once without performing irradiation on a group of spots multiple times separately (or without interrupting and restarting the irradiation). In addition, an unexpected gap between spots and unexpected overlapped spots are not formed. A desired dose distribution of beams with which a group of spots is irradiated can be formed.

According to the present invention, even when a failure occurs, irradiation is continuously performed depending on the type or level of the cause of the failure. From the perspective of safety of a patient and an operator, it is very important to specify the type and level of the cause in which continuous irradiation would be possible.

According to the present invention, even when a relatively minor failure occurs during irradiation of a certain spot or the respiratory gating signal is turned off, the irradiation is continuously performed on a group that includes the certain spot. Thus, it is unnecessary that the irradiation be performed on the spot group multiple times separately (or it is unnecessary that the irradiation be interrupted and restarted). The irradiation is reliably performed on the spot group once so that an irradiation dose distribution can be appropriately controlled.

Since it is possible to suppress an operation of irradiating a group of spots multiple times separately (or it is possible to suppress an operation of interrupting and restarting the irradiation), the treatment time is reduced and the system is efficiently operated.

BRIEF DESCRIPTION OF THE DRAWINGS

FIG. 5 is a diagram showing a part of treatment plan information generated by a treatment plan unit shown in FIG. 1 and contents of command signals that are used to perform scanning irradiation on each layer.

DESCRIPTION OF THE PREFERRED EMBODIMENTS

A charged particle irradiation system according to an embodiment of the present invention is described below in detail with reference to the accompanying drawings.

Figure 1:
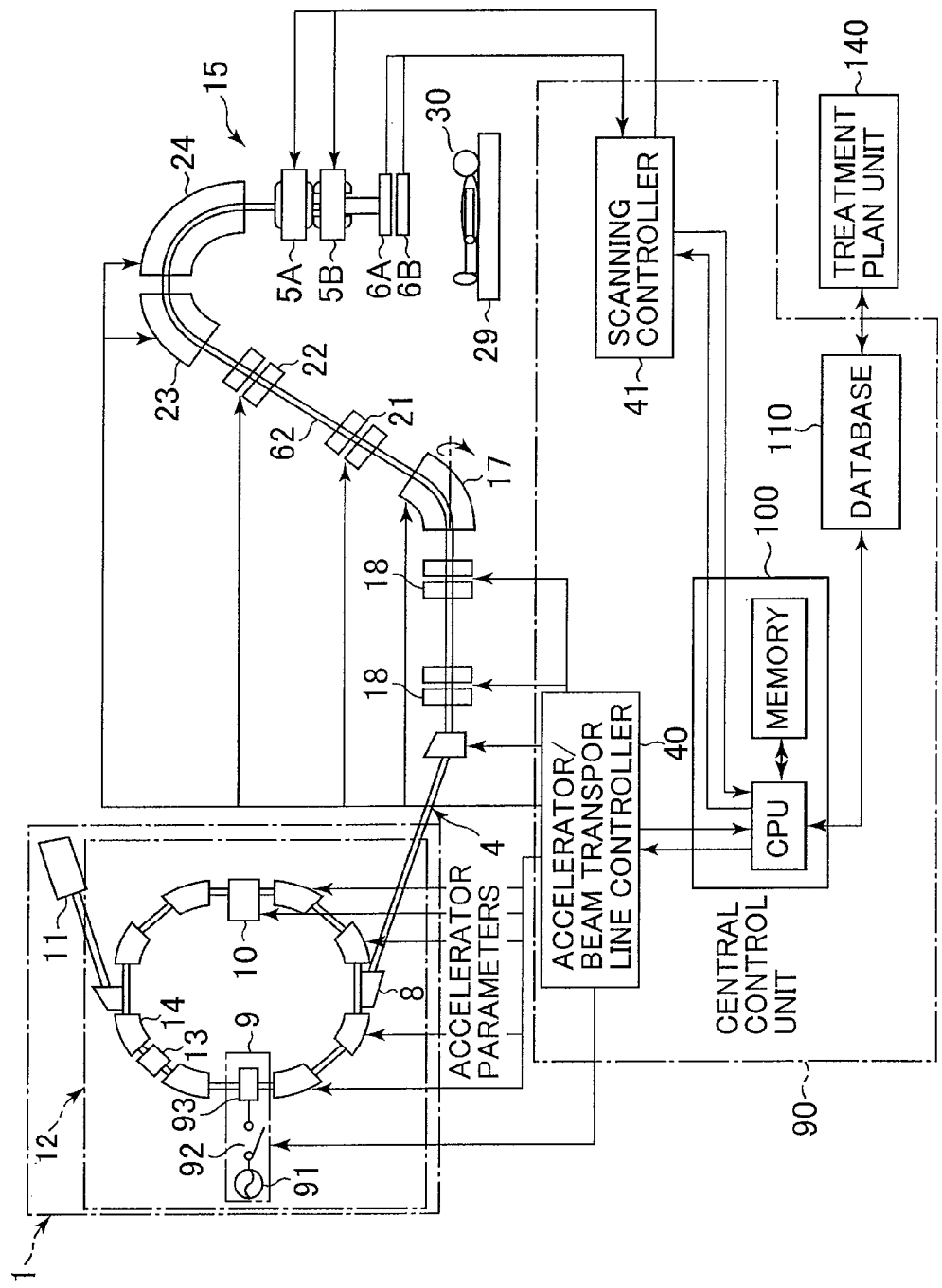
FIG. 1 is a conceptional diagram showing the entire configuration of a proton beam irradiation system that serves as a charged particle irradiation system according to an embodiment of the present invention.
Figure 2:
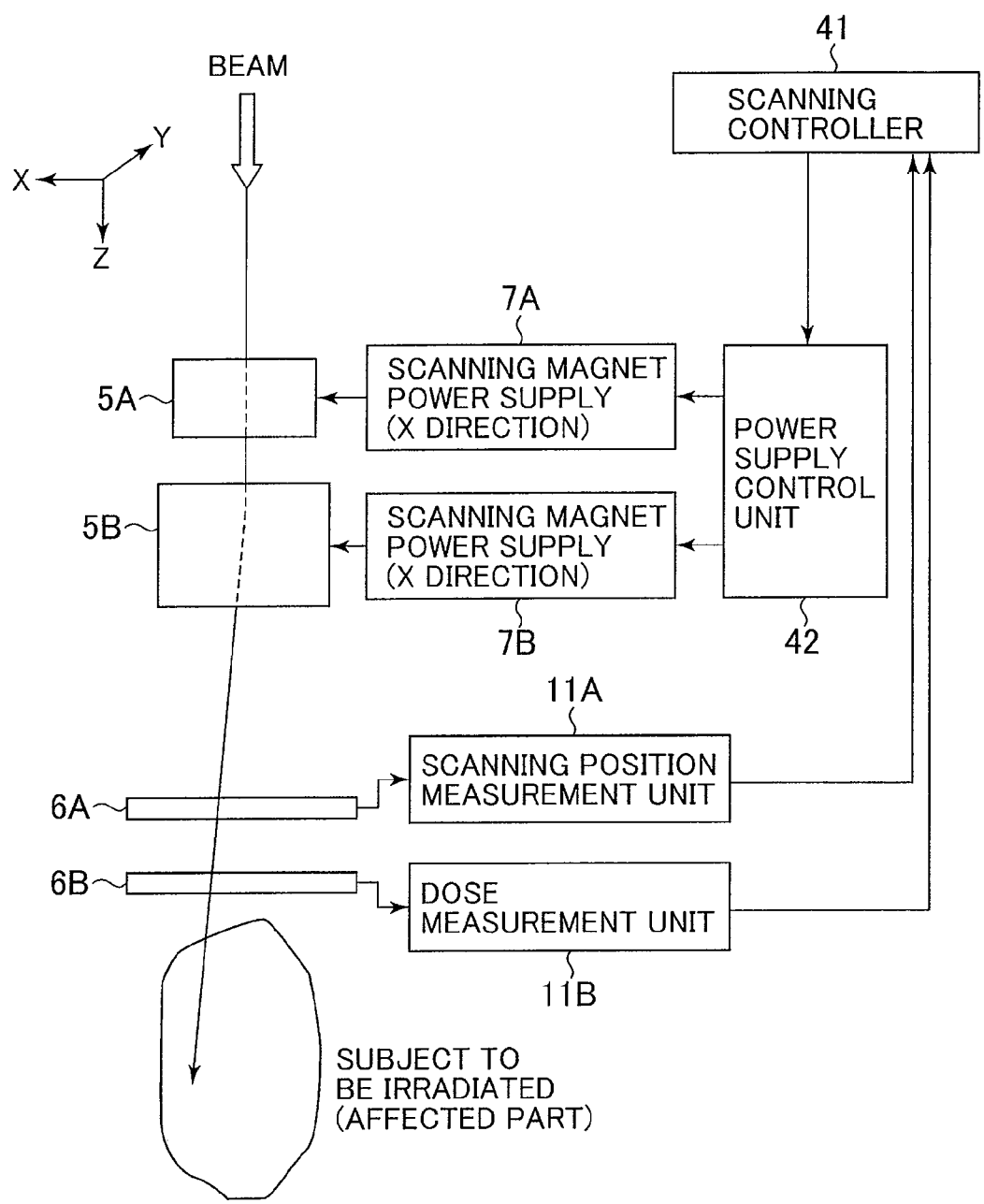
FIG. 2 is a conceptional diagram showing in detail a scanning irradiation unit included in the proton beam irradiation system that serves as the charged particle irradiation system according to the embodiment of the present invention.

FIG. 1 is a conceptional diagram showing a proton beam irradiation system that serves as the charged particle irradiation system according to the embodiment of the present invention. FIG. 2 is a conceptional diagram showing a scanning irradiation unit that constitutes a part of the charged particle irradiation system according to the embodiment of the present invention.

Referring to FIG. 1, the charged particle irradiation system irradiates, with a charged particle beam (e.g., proton beam), an affected part of a patient who is fixed to a treatment bed placed in a treatment room. The charged particle irradiation system treats the affected part. The charged particle irradiation system includes an ion beam generator 1, a beam transport line 4, a scanning irradiation unit 15, and a control system 90. The beam transport line 4 is connected to the ion beam generator 1 on a downstream side of the ion beam generator 1. The scanning irradiation unit 15 is connected to the beam transport line 4 and irradiates the affected part of the patient with the charged particle beam. The control system 90 controls the ion beam generator 1, the beam transport line 4, and the scanning irradiation unit 15 on the basis of a treatment plan.

The ion beam generator 1 includes an ion source (not shown), a pre-stage ion beam generator (linear accelerator) 11, and a synchrotron (accelerator) 12. The synchrotron 12 includes a radiofrequency acceleration system 9 and an acceleration system 10. The radiofrequency acceleration system 9 includes an extraction radiofrequency electrode 93, an extraction radiofrequency power supply 91, and a switch 92. The extraction radiofrequency electrode 93 is arranged on a circular trajectory of the synchrotron 12. The extraction radiofrequency electrode 93 and the extraction radiofrequency power supply 91 are connected to each other by the switch 92.

The acceleration system (charged particle beam energy changing system) 10 has a radiofrequency acceleration cavity (not shown) and a radiofrequency power supply (not shown). The radiofrequency acceleration cavity is arranged on the circular trajectory. The radiofrequency power supply applies radiofrequency power to the radiofrequency acceleration cavity.

Ions (e.g., proton ions (or carbon ions)) are generated by the ion source and accelerated by the pre-stage ion beam generator (e.g., linear ion beam generator) 11 to form an ion beam.

The ion beam (proton beam) is extracted from the pre-stage ion beam generator 11 and injected into the synchrotron 12.

The ion beam that is a charged particle beam passes through the radiofrequency power supply and the radiofrequency acceleration cavity in this order in the synchrotron 12. In this case, radiofrequency power is applied to the ion beam so that the ion beam receives energy and is accelerated in the synchrotron 12.

The energy of the ion beam that circulates in the synchrotron 12 is increased to set energy (e.g., 100 to 200 MeV). After that, a radiofrequency wave for extraction is transmitted from the extraction radiofrequency power supply 91 through the switch 92 that is in a closed state, and reaches the extraction radiofrequency electrode 93. Then, the extraction radiofrequency electrode 93 applies the radiofrequency wave to the ion beam.

The ion beam circulates within a stability limit before the radiofrequency wave is applied to the ion beam. After the radiofrequency wave is applied to the ion beam, the ion beam moves beyond the stability limit. Then, the ion beam is extracted from the synchrotron 12 through an extraction deflector 8. During the process of extracting the ion beam, currents that are applied to a quadrupole magnet 13 and a bending magnet 14 are maintained at set values, and the stability limit is maintained at an almost constant level. The quadrupole magnet 13 and the bending magnet 14 are included in the synchrotron 12.

When the switch 92 is opened to stop applying the radiofrequency wave to the extraction radiofrequency electrode 93, the extraction of the ion beam from the synchrotron 12 is stopped.

The ion beam extracted from the synchrotron 12 is transported toward a downstream side by the beam transport line 4. The beam transport line 4 includes a quadrupole magnet 18, a bending magnet 17, a quadrupole magnet 21, a quadrupole magnet 22, a bending magnet 23, and a bending magnet 24. The quadrupole magnet 21, the quadrupole magnet 22, the bending magnet 23, and the bending magnet 24 are located on a beam path 62 on an upstream side with respect to the direction of propagation of the beam. The beam path 62 is connected to the scanning irradiation unit 15 that is located in the treatment room. The ion beam introduced into the beam transport line 4 is transported to the scanning irradiation unit 15 through the beam path 62.

A rotating gantry (not shown) is provided in the treatment room. The scanning irradiation unit 15 and a part of the beam transport line 4 are included in a substantially cylindrical rotating cylinder (not shown) of the rotating gantry. The rotating cylinder can be rotated by a motor (not shown). A treatment gauge (not shown) is provided in the rotating cylinder.

An injected beam position monitor (not shown), scanning magnets 5A and 5B, a beam position monitor 6A, a dose monitor 6B and the like are arranged in a casing (not shown) of the scanning irradiation unit 15 in this order from the upstream side with respect to the direction (downward direction in FIGS. 1 and 2, and a Z direction in FIG. 2) of the propagation of the beam. The injected beam position monitor detects the position of the injected beam. The scanning magnets 5A and 5B deflect the beam so that the beam is scanned over the affected part. The beam position monitor 6A detects the position of a spot of the deflected beam. The dose monitor 6B detects the dose of the beam which is scanned over the affected part.

The scanning magnets 5A and 5B apply magnetic fields to the beam in X and Y directions and thereby deflect the beam so that a point to be irradiated is moved in the X and Y directions. The X and Y directions are parallel to a flat plane perpendicular to the beam axis (direction of the propagation of the beam) and are perpendicular to each other.

As shown in FIG. 2, the scanning magnet 5A is connected to scanning magnet power supply 7A, while the scanning magnet 5B is connected to scanning magnet power supply 7B. A power supply control unit 42 controls currents that are supplied from the scanning magnet power supply 7A and 7B to the scanning magnets 5A and 5B. In this case, the power supply control unit 42 controls, on the basis of a control signal transmitted from a scanning irradiation control unit 41, the currents that are supplied to the scanning magnets 5A and 5B. The power supply control unit 42 controls excited magnetic fields generated by the scanning magnets 5A and 5B. The charged particle beam is deflected by the excited magnetic fields (controlled in the aforementioned manner) generated by the scanning magnets 5A and 5B.

The beam position monitor 6A detects whether or not the position (hereinafter referred to as a beam scanning position) of the spot of the beam deflected by the scanning magnets 5A and 5B is a controlled position (set value). The beam position monitor 6A obtains a signal (detection signal) indicative of the result of the detection and outputs the detection signal to a scanning position measurement unit 11A. The scanning position measurement unit 11A calculates the beam scanning position on the basis of the detection signal. The scanning position measurement unit 11A outputs data on the result of the calculation to the scanning irradiation control unit 41.

The dose monitor 6B detects the dose of the beam that has been detected by the beam position monitor 6A and has formed the spot at the beam scanning position. The dose monitor 6B outputs a signal (detection signal) indicative of the detected dose to a dose measurement unit 11B. The dose measurement unit 11B calculates the dose on the basis of the detection signal. The dose measurement unit 11B outputs data on the result of the calculation to the scanning irradiation control unit 41.

The beam position monitor 6A and the dose monitor 6B form an irradiation dose detecting unit that measures the dose of the charged particle beam (with which the subject is irradiated) and a dose distribution.

Returning to FIG. 1, the treatment bed 29 is moved by a bed driving unit (not shown), placed in the treatment gauge, and positioned for irradiation to be performed by the scanning irradiation unit 15 before the irradiation with the ion beam injected from the scanning irradiation unit 15. The rotating cylinder is rotated by rotation (controlled by a gantry controller (not shown)) of the motor so that the beam propagates toward the affected part of the patient.

The ion beam passes through the beam path 62 and is introduced from the beam transport line (formed in a reversed U-shape) into the scanning irradiation unit 15. Then, the ion beam is deflected by the scanning magnets (charged particle beam scanning units) 5A and 5B. Then, the affected part (e.g., a part with cancer or tumor) of the patient 30 is irradiated with the ion beam. The ion beam with which the affected part is irradiated emits energy at the affected part and forms a high dose region.

The charged particle irradiation system according to the present embodiment has a control system 90. The control system 90 is described below with reference to FIGS. 1 and 2.

The control system 90 includes a database 110, an accelerator/transport line controller (hereinafter referred to as an accelerator controller) 40, the scanning irradiation control unit (hereinafter referred to as a scanning controller) 41, a central control unit 100. Treatment plan data is generated by a treatment plan unit 140 and stored in the database 110. The accelerator controller 40 controls the ion beam generator 1 and the beam transport line 4. The scanning controller 41 controls the scanning irradiation unit 15. The central control unit 100 controls the accelerator controller 40 and the scanning controller 41 on the basis of the treatment plan data read from the database 110.

The treatment plan information (patient information) stored in the database 110 is provided for each patient. The treatment plan information includes a patient identification number, the irradiation dose (for one time of irradiation), an irradiation energy value, an irradiation direction, and the position of a point to be irradiated, which are not shown in the drawings.

The central control unit 100 reads, from the database 110, the treatment plan information on the patient 30 (to be treated) on the basis of patient identification information input from an input device such as a keyboard or a mouse. A control pattern of supplying excited power to each of the aforementioned magnets is determined based on the irradiation energy value included in the treatment plan information for each patient.

A power supply control table is pre-stored in a memory included in the central control unit 100. The values or pattern of the excited power that is to be applied to the quadrupole magnet 13, the bending magnet 14, the quadrupole magnet 18, the bending magnet 17, the quadrupole magnets 21, 22, and the bending magnets 23, 24 are or is determined on the basis of the values (70, 80, 90, . . . , MeV and the like) of the irradiation energy. The quadrupole magnet 13 and the bending magnet 14 are included in the ion beam generator 1 that includes the synchrotron 12. The quadrupole 18, the bending magnet 17, the quadrupole 21, 22, and the bending magnets 23, 24 are included in the beam transport line 4.

The central control unit 100 has therein a CPU that generates control command data (control command information) on the patient (to be treated) using the treatment plan information and the power supply control table. The control command data is used to control the magnets included in the ion beam generator 1 and the magnets included in the beam path 62. The generated control command data is output to the scanning controller 41 and the accelerator controller 40.

In the proton beam irradiation system according to the present embodiment, the central control unit 100, the scanning controller 41, and the accelerator controller 40 cooperate with each other to perform control on the basis of the treatment plan information generated by the treatment plan unit 140. The control that is performed by the central control unit 100, the scanning controller 41, and the accelerator controller 40 is described below.

Figure 3:
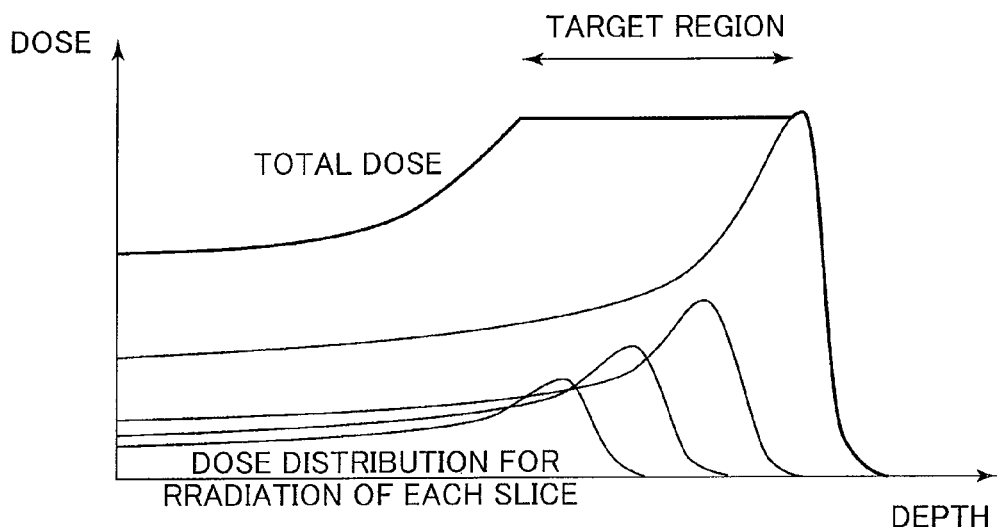
FIG. 3 is a conceptional diagram showing an example of a distribution of doses of beams with which layers of an affected part are irradiated in order to ensure uniformity of the dose distribution.

First, the relationship between the depth of an irradiation target and the energy of the ion beam (charged particle beam) is described. The irradiation target is a region that includes the affected part and is irradiated with the ion beam. The irradiation target is slightly larger than the affected part. FIG. 3 shows an example of the relationship between the depth of the inside of the body of the patient and the dose of the ion beam. When the charged particle beam loses energy and stops, the beam provides a large amount of energy to the surrounding of the beam. Thus, the dose of the beam is peaked at a depth location that the beam reaches. The peak of the dose is called a Bragg peak.

The target is irradiated with the ion beam at the location at which the dose is at the Bragg peak. The location at which the dose is at the Bragg peak varies depending on the energy of the ion beam. The entire target (target region) that has a thickness in the direction (depth direction) of the depth of the inside of the body can be uniformly irradiated with the ion beam by dividing the target into a plurality of layers (slices) in the depth direction (direction of propagation of the ion beam in the body) and changing the energy of the ion beam on the basis of the depth (each layer). The treatment plan unit 140 determines, on the basis of the aforementioned viewpoint, the number of the layers that are obtained by dividing the target region in the depth direction.

Figure 4:
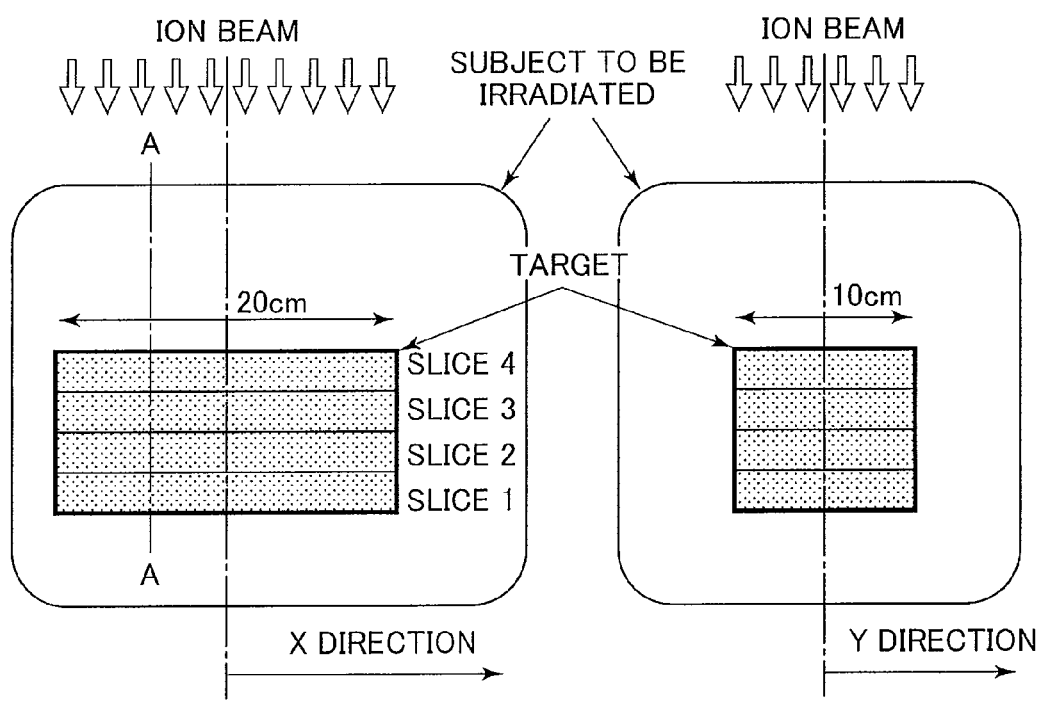
FIG. 4 is a diagram showing an example of the layers of the affected part that is to be irradiated by the charged particle irradiation system shown in FIG. 1.

FIG. 4 is a diagram showing an example of the layers determined in the aforementioned manner. In this example, the affected part is divided into four layers 1, 2, 3, and 4 that are arranged in this order from the lowest layer to the top layer that is the closest to the surface of the body of the patient 30. In the example, each of the layers has a length of 20 cm in the X direction and a length of 10 cm in the Y direction. The abscissa of FIG. 3 that shows the dose distribution indicates the depth direction of a cross section A-A' of FIG. 4.

After the number of the layers is determined, the treatment plan unit 140 determines the number of spots (points to be irradiated) arranged in a direction perpendicular to the depth direction in each of the layers (target cross sections).

Fractionated irradiation is performed on each of all the spots a plurality of times in some cases. The number of times of irradiation of each spot and the dose (target dose) of the beam for one time of irradiation are determined so that a variation in the dose of the beam for irradiation of each spot is in a certain range and the dose distribution is almost constant in the entire target region. The concept of the fractionated irradiation is described in detail in Japanese Patent No. 3681744.

The treatment plan information that is generated in the aforementioned manner and stored in the database 110 is read by the central control unit 100 and stored in the memory of the central control unit 100. The CPU of the central control unit 100 generates, on the basis of the treatment plan information stored in the memory, information (the number of layers, the number (number of spots) of points to be irradiated, points to be irradiated in each layer, a target irradiation dose (set irradiation dose) of the beam with which the points are to be irradiated, values of currents to be applied to the scanning magnets 5A and 5B for irradiation of all the spots in each of the layers, and the like) on irradiation with the ion beam. Then, the CPU of the central control unit 100 transmits the generated information to the scanning controller 41 (first control unit).

A part of the transmitted treatment plan information is shown in FIG. 5. The part of the treatment plan information includes: the position (in the X direction) of each of the points (spots) to be irradiated in each of the layers; the position (in the Y direction) of each of the points (spots) to be irradiated in each of the layers; the target irradiation dose (set dose) of the beam with which each of the points is to be irradiated; a layer (slice) changing flag for each of the points to be irradiated; and a spot number for each of the points to be irradiated. The spot number indicates the order of the irradiation of the points (spots). In addition, an irradiation interrupt-enabled flag is provided for each of the spots and included in the treatment plan information (0 indicates that the irradiation cannot be interrupted; and 1 indicates that the irradiation can be interrupted). In the present embodiment, the irradiation is performed in order from the lowest (deepest) layer to the top layer that is the closest to the surface of the body of the patient. The target irradiation dose (set dose) of the beam with which each of the points are to be irradiated is equal to the irradiation dose accumulated from the time when the affected part is first irradiated. The central control unit 100 sequentially calculates the irradiation dose set for each of the points to be irradiated and generates information on the target irradiation dose. Then, the central control unit 100 transmits the generated information to the scanning controller 41. The scanning controller 41 stores the treatment plan information in a memory included in the scanning controller 41.

FIG. 5 shows the example in which fractionated irradiation is not performed. When fractionated irradiation is performed, the following information is necessary and included in the treatment plan information shown in FIG. 5: the positions (in the X direction) of the points (spots) to be irradiated, which are provided for the times of the fractionated irradiation; the positions (in the Y direction) of the points to be irradiated, which are provided for the times of the fractionated irradiation; and target irradiation doses (set doses) of the beams (with which the points are irradiated), which are provided for the times of the fractionated irradiation.

The CPU of the central control unit 100 transmits, to the accelerator controller 40, all accelerator parameters for the synchrotron 12 that are included in the treatment plan information and provided for all the layers. The transmitted accelerator parameters are classified into multiple acceleration patterns.

Figure 6:
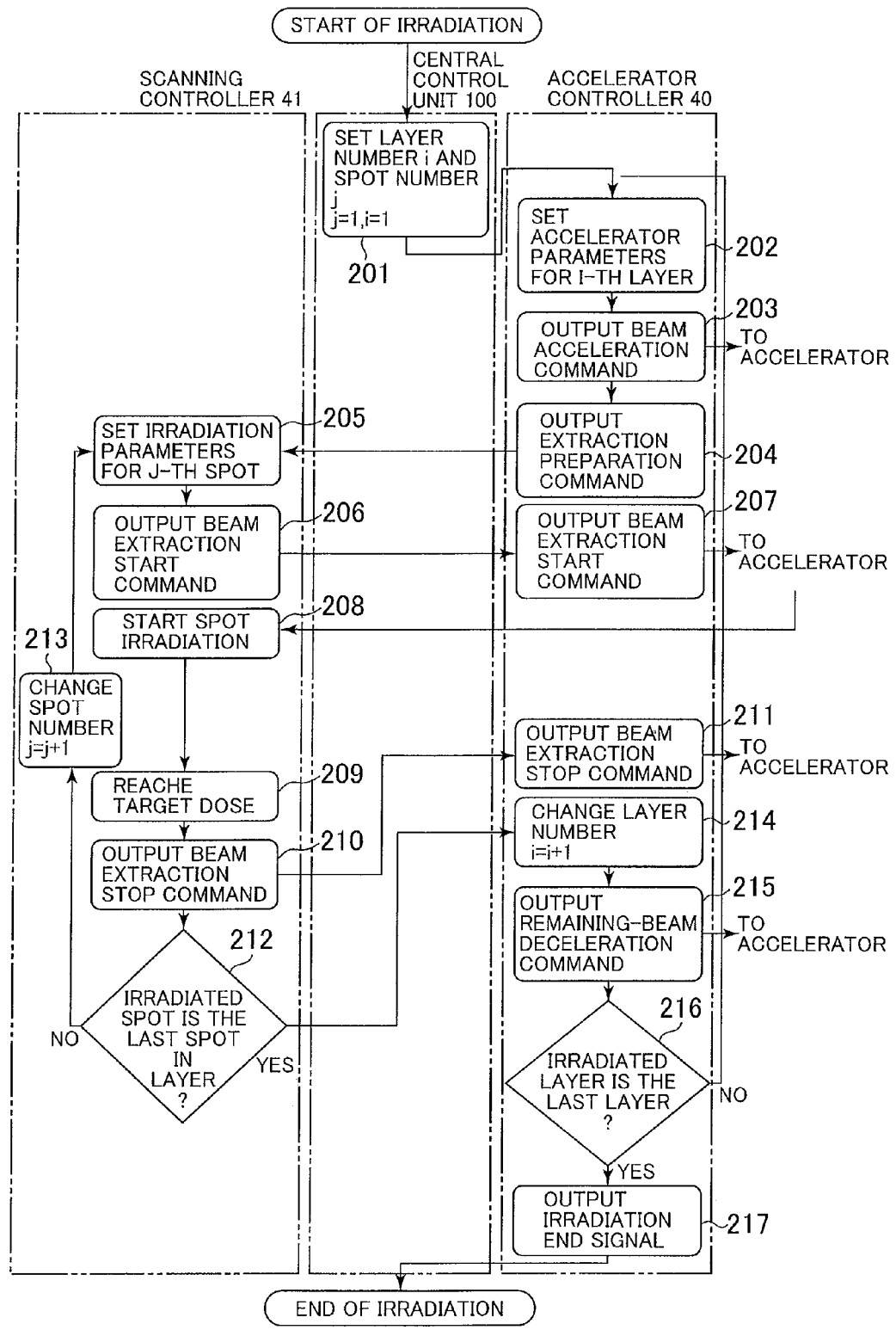
FIG. 6 is a flowchart of an example of control operations to be performed by a control system (that includes a central control unit, a scanning controller, and an accelerator controller) shown in FIG. 1 during normal irradiation.

The following describes, with reference to FIG. 6, normal control operations of the central control unit 100, the scanning controller 41, and the accelerator controller 40 during spot scanning irradiation in the case where an irradiation interruption cause does not occur in the present embodiment. FIG. 6 is a flowchart of an example of the control operations.

First, when an irradiation start instruction unit (not shown) located in the treatment room is operated, the central control unit 100 initially sets operators i and j to 1 and outputs the operators i and j to the accelerator controller 40 on the basis of the operation of the irradiation start instruction unit in step 201. The operator i indicates a layer number, and the operator j indicates a spot number.

The accelerator controller 40 performs initial setting in response to the operators. After the initial setting, the accelerator controller 40 reads accelerator parameters for the i-th layer (i=1 at this time) from the accelerator parameters that are stored in the memory and classified into the multiple patterns, and sets the read accelerator parameters in step 202.

In step 203, the accelerator controller 40 outputs the set parameters to the synchrotron 12 and the beam transport line 4. In addition, the accelerator controller 40 controls each magnet power supply so that each magnet is excited by a current with a set predetermined amount. Furthermore, the accelerator controller 40 controls the radiofrequency power supply that applies radiofrequency power to the radiofrequency acceleration cavity so that the radiofrequency power and a frequency are increased to predetermined values.

When the energy of the ion beam that circulates in the synchrotron 12 is increased to a value set in the treatment plan, the accelerator controller 40 outputs an extraction preparation command to the scanning controller 41 through the central control unit 100 in step 204.

The scanning controller 41 (first control unit) receives the extraction preparation command. In response to the received extraction preparation command, the scanning controller 41 reads current value data and target irradiation dose data for the j-th spot (j=1 at this time) from the current value data (included in the fields of "Position in X direction" and "Position in Y direction" shown in FIG. 5) stored in the memory and the target irradiation dose data (included in the fields of "Target irradiation dose" shown in FIG. 5) stored in the memory, and sets the read data in step 205. In this case, the scanning controller 41 controls the power supply 7A and 7B so that the scanning magnets 5A and 5B are excited by means of the current values for the j-th spot.

After the preparation for irradiation of the spot is completed, the scanning controller 41 outputs a beam extraction start command to the accelerator controller 40 (third control unit) through the central control unit 100 in step 206.

In response to the beam extraction start command, the accelerator controller 40 controls the radiofrequency acceleration system 9 and causes the ion beam to be extracted from the synchrotron 12 in step 207. Specifically, the switch 92 is closed by the beam extraction start command output from the accelerator controller 40 so that the radiofrequency wave is applied to the ion beam by the extraction radiofrequency electrode 93 and the ion beam is extracted from the synchrotron 12.

Since the scanning magnets 5A and 5B are excited so that the ion beam reaches the j-th spot, the j-th spot located in the layer is irradiated with the ion beam by the scanning irradiation unit 15 in step 208.

The j-th spot (point to be irradiated) is detected by the beam position monitor 6A. The beam scanning position is calculated by the scanning position measurement unit 11A. The dose of the beam with which the j-th spot is irradiated is detected by the dose monitor 6B. The dose is calculated by the dose measurement unit 11B. The measurement unit 11A and 11B output the calculation results to the scanning controller 41.

The scanning controller 41 compares the set target irradiation dose with the received calculation results in step 209. As a result, when the dose of the beam with which the j-th spot is irradiated reaches the target irradiation dose, the scanning controller 41 outputs a beam extraction stop command to the accelerator controller 40 through the central control unit 100 in step 210.

In response to the beam extraction stop command, the switch 92 is opened by the accelerator controller 40 so that the extraction of the ion beam is stopped.

In this manner, after the first spot is irradiated, the scanning controller 41 determines whether or not the irradiated spot is the last spot in the layer in step 212. If the answer is negative (No) in step 212, the scanning controller 41 adds 1 to the spot number (or the point to be irradiated is changed to the next spot) in step 213.

Then, steps 205 to 213 are repeated. Specifically, until irradiation of all spots located in the first layer is completed, the scanning magnets 5A and 5B sequentially deflect the ion beam so that a spot adjacent to the irradiated spot is sequentially irradiated (spot scanning irradiation) with the ion beam, while the irradiation of the ion beam is stopped during the deflection of the ion beam.

When the irradiation of all the spots located in the first layer is completed, the answer is affirmative (Yes) in step 212, and the scanning controller 41 outputs a layer change command to the accelerator controller 40 through the central control unit 100.

When the fractionated irradiation is performed, the following process is performed before the layer change command is output in step 212. In the process, the operator j that indicates the spot number is initially set to 1; it is determined whether or not an operator n that indicates the number of times of fractionated irradiation reaches a preset fractionated irradiation number; if the answer is negative (No), 1 is added to the operator (irradiation number) n (or a fractionated irradiation number is changed to the next number); steps 205 to 213 are repeated; and when the irradiation number n that indicates the number of times of the fractionated irradiation reaches the preset fractionated irradiation number, the scanning controller 41 outputs the layer change command to the accelerator controller 40 in step 212.

After the scanning controller 41 outputs the layer change command, the accelerator controller 40 receives the layer change command. In response to the layer change command, the accelerator controller 40 adds 1 to the layer number i (or the point to be irradiated is changed to a point in the second layer) in step 214 and outputs a beam deceleration command to the synchrotron 12 in step 215.

After the output of the beam deceleration command, the accelerator controller 40 controls the power supply for each magnet included in the synchrotron 12, gradually reduces an excitation current (that is applied to each magnet), and finally sets the excitation current to a predetermined value, for example, a value that is suitable for next injection of the ion beam. Thus, the ion beam that circulates in the synchrotron 12 is decelerated.

At that point of time, the first layer is simply irradiated. Thus, the answer is negative (No) in step 216 and the process returns to step 202. Then, steps 203 to 215 are repeated for the second layer.

Similarly, steps 202 to 215 are performed for all the layers. After that, the accelerator controller 40 determines that the irradiated layer is the last layer (the answer is affirmative (Yes)) in step 216. Thus, the irradiation of all the spots located in all the layers of the affected part of the patient 30 is completed. Then, the accelerator controller 40 outputs an irradiation end signal to the CPU of the central control unit 100.

Then, a series of the irradiation processes on the affected part of the patient 30 are ended.

Next, a control process (censoring process that is performed on the basis of a spot group), which is a feature of the present embodiment, is described.

The control system 90 according to the present embodiment has an interlock. The interlock monitors a failure that occurs in the system and the constituent devices. In addition, the interlock monitors the state of the beam that is present in the accelerator. When a failure occurs in the system or any of the constituent devices, the interlock stops or interrupts the irradiation on the basis of the type or level of the cause of the failure.

An operator can use an irradiation stop instruction unit (not shown) or an irradiation interrupt instruction unit (not shown) to manually stop or interrupt the irradiation at the discretion of the operator. The irradiation stop instruction unit and the irradiation interrupt instruction unit are located in the treatment room.

Figure 7:
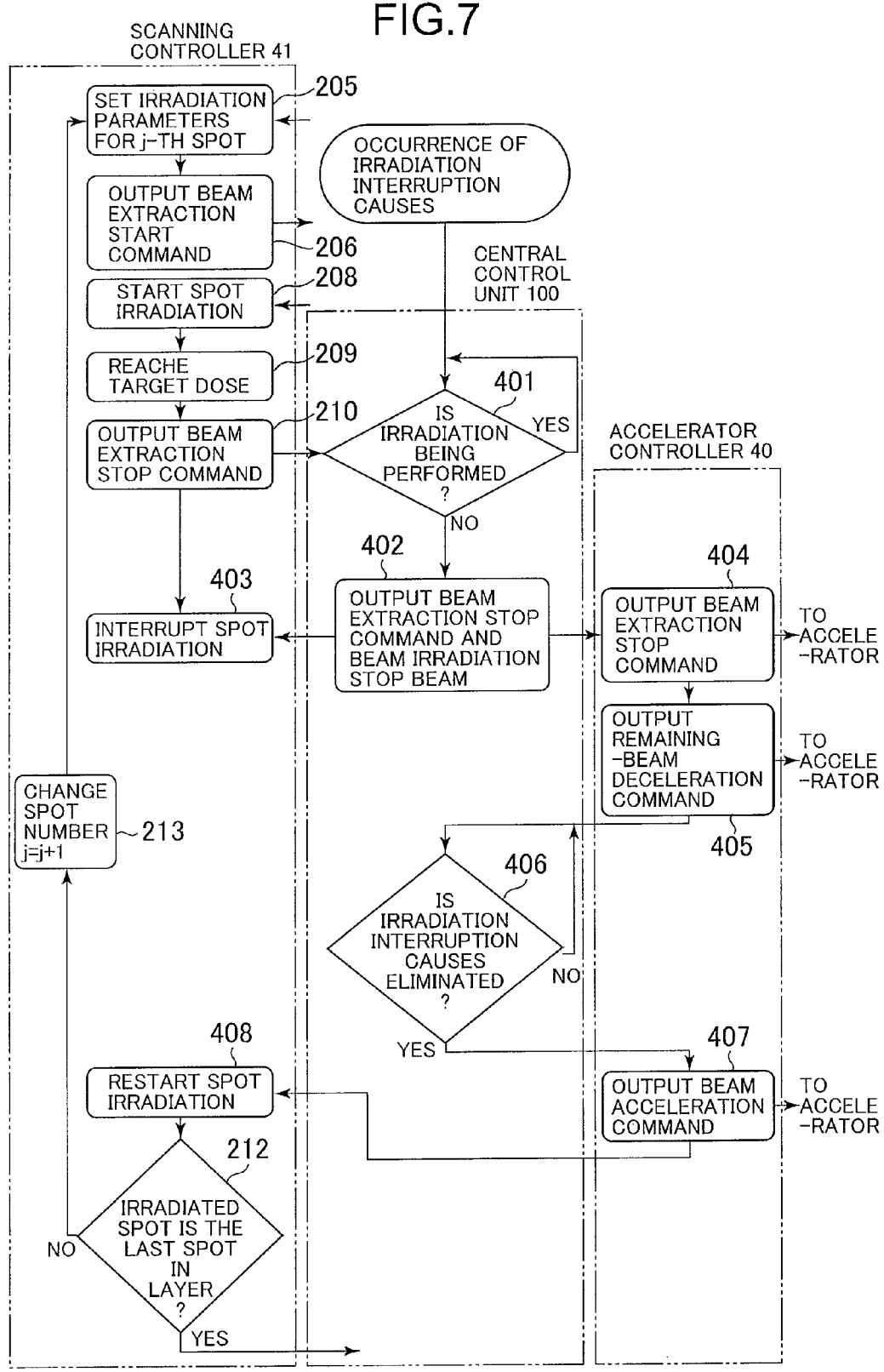
FIG. 7 is a flowchart of an example of control operations to be performed by a control system (that includes a central control unit, a scanning controller, and an accelerator controller) included in a conventional system when an event that causes interruption of spot irradiation occurs during the spot irradiation.
Figure 8:
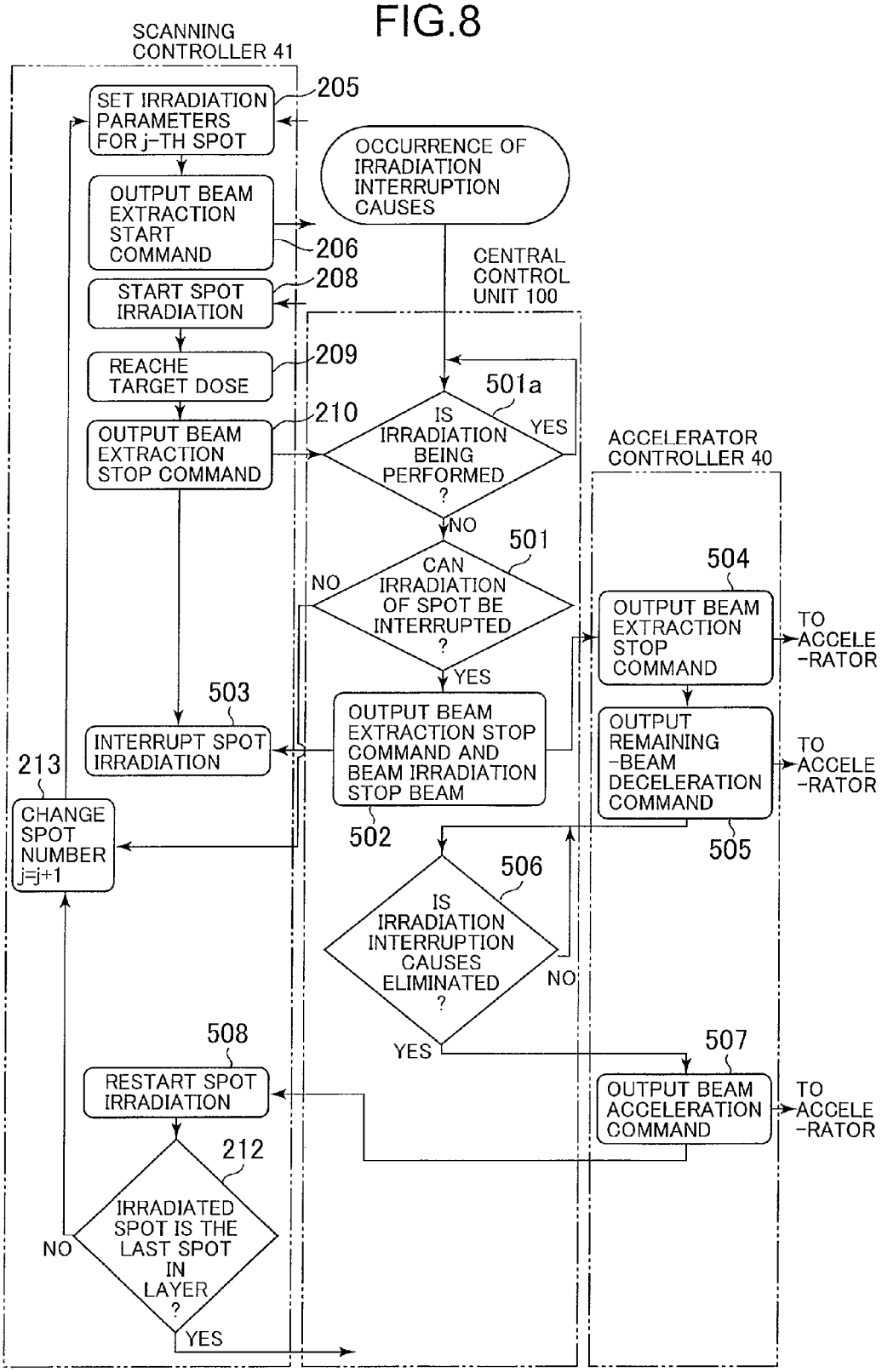
FIG. 8 is a flowchart of an example of control operations to be performed by the control system (that includes the central control unit, the scanning controller, and the accelerator controller) shown in FIG. 1 when an event that causes interruption of spot irradiation occurs during the spot irradiation in the embodiment of the present invention.

The present embodiment focuses on the method for stopping the extraction of the ion beam when an irradiation interruption cause occurs during the irradiation of a certain spot or during a time period between the end of the irradiation of a certain spot and the start of the irradiation of the next spot. FIG. 7 is a flowchart of control operations that are performed by a conventional system and described for comparison. FIG. 8 is a flowchart of control operations that are performed by the system according to the present embodiment. In normal operations, both systems perform processes on the basis of the control operations described with reference to FIG. 6.

The control process according to the present invention handles irradiation interruption causes among irradiation stop causes and irradiation interruption causes, which occur due to a failure in the system and the constituent devices and the state of the beam present in the accelerator. The causes handled by the control process according to the present invention are limited to relatively minor causes in which continuous irradiation would be possible. FIG. 7 is the flowchart of the control operations to be performed by the conventional system when an irradiation interruption cause occurs during irradiation of a certain spot.

In the conventional system, when an irradiation interruption cause occurs during irradiation, a central control unit 100 (included in the conventional system) receives an irradiation interruption command and determines whether or not any of spots is being irradiated in step 401. In this case, the central control unit 100 can easily make the determination by confirming whether or not a scanning controller 41 (included in the conventional system) outputs a beam extraction stop command in step 210.

If the answer is affirmative (Yes) in step 401 (or when an irradiation interruption cause occurs during the irradiation of the certain spot), the central control unit 100 stops a subsequent irradiation interruption process until the central control unit 100 determines that all the spots are not being irradiated in step 401. If the answer is negative (No) in step 401 (or when an irradiation interruption cause occurs during irradiation other than the irradiation of the certain spot or when an irradiation interruption cause occurs during the irradiation of the certain spot and the irradiation of the certain spot is terminated after the occurrence of the irradiation interruption cause), the central control unit 100 outputs a beam extraction stop command to an accelerator controller 40 (included in the conventional system) and outputs a beam irradiation stop command to the scanning controller 41 in step 402.

The scanning controller 41 receives the beam irradiation stop command and interrupts a process of irradiating the subsequent j-th spot (after step 210 is performed).

The accelerator controller 40 stops the extraction of the beam from the synchrotron 12 in step 404. After that, the accelerator controller 40 outputs a remaining beam deceleration command to the synchrotron 12 and decelerates the beam that remains in the synchrotron 12.

When an event that causes the irradiation to be interrupted occurs during the irradiation of the certain spot (point to be irradiated), the central control unit 100 (second control unit) continuously controls the scanning controller 41 (first control unit) until the dose of the beam with which the spot is irradiated reaches a target dose. The central control unit 100 interrupts the control of the scanning controller 41 when the dose of the beam with which the spot is irradiated reaches the target dose. Also, the central control unit 100 stops the extraction of the charged particle beam from the synchrotron (accelerator) 12.

The central control unit 100 determines whether or not the irradiation interruption cause is eliminated and the irradiation can be restarted in step 406. If the answer is affirmative (Yes) in step 406, the accelerator controller 40 outputs a beam acceleration command to the synchrotron 12 in step 407. Then, the accelerator controller 40 controls each magnet power supply so that each magnet is excited by a current with a set predetermined amount again. In addition, the accelerator controller 40 controls radiofrequency power supply that applies radiofrequency power to a radiofrequency acceleration cavity so that the radiofrequency power and a frequency are increased to predetermined values.

Simultaneously with the aforementioned control, the acceleration controller 40 outputs a recovery command to the scanning controller 41. When the scanning controller 41 receives the recovery command, the scanning controller 41 restarts the interrupted irradiation process on the j-th spot in step 408. However, since the dose of the beam with which the j-th spot is irradiated reaches the target dose (in step 209) in the conventional system, the irradiation process on the j-th spot is immediately terminated. The scanning controller 41 determines whether or not the spot is the last spot in the layer in step 212. If the answer is negative (No) in step 212, the scanning controller 41 adds 1 to the spot number (or the point to be irradiated is changed to the next spot) in step 213. Then, the scanning controller 41 performs steps 205 and 206. In steps 205 and 206, the scanning controller 41 controls scanning magnets (charged particle beam scanning units) 5A and 5B included in a scanning irradiation unit 15 to cause the scanning magnets to change the spot (point to be irradiated) and restarts the extraction of the charged particle beam from the synchrotron 12 (accelerator) after the change of the spot. After that, each step is repeated in the same manner as the normal operations. Then, a series of the irradiation processes on the affected part of the patient 30 are ended.

When the extraction of the charged particle beam is stopped by the accelerator controller 40 through steps 402 and 404 and an event that causes the irradiation to be interrupted is eliminated after the stop of the extraction, the central control unit 100 (second control unit) recovers the control of the scanning controller 41 (first control unit) through steps 407 and 408. After the recovery, the scanning controller 41 immediately controls the scanning magnets 5A and 5B (charged particle beam scanning units) to cause the scanning magnets 5A and 5B to change the spot (point to be irradiated) and restarts the extraction of the charged particle beam from the synchrotron 12 (accelerator) after the change of the spot.

In the conventional system, when an irradiation interruption cause occurs during the irradiation of a certain group of spots, the extraction (irradiation with the beam) of the beam is stopped after completion of the irradiation of the spot. Thus, irradiation is forcibly performed on the group of spots two or more times separately before the completion of the irradiation of the group of spots. As a result, the spots that are secondarily irradiated are misaligned with the spots that are first irradiated, and an irradiation distribution may be inappropriate (slight misalignment of a device included in the system and slight misalignment of the patient are considered as the cause of the misalignment).

A feature of the present embodiment is described below. In the present embodiment, when an irradiation interruption cause occurs during the irradiation of a certain group of spots, the extraction (irradiation with the beam) of the beam is stopped after all the spots included in the certain group are irradiated without immediately stopping the extraction of the beam. Thus, the irradiation is not stopped during the irradiation of the certain group of spots.

The following describes operations of the control system according to the present embodiment when an irradiation interruption cause occurs during the irradiation of a certain group of spots. FIG. 8 is a flowchart of the control operations to be performed by the control system according to the present embodiment when an irradiation interruption cause occurs during the irradiation of a certain group of spots.

In the present embodiment, when an irradiation interruption cause occurs during the irradiation and the central control unit 100 receives an irradiation interruption command, the central control unit 100 determines whether or not any of the spots (included in the certain group) is being irradiated in step 501a. In this case, the central control unit 100 can easily make the determination by confirming whether or not the scanning controller 41 outputs a beam extraction stop command in step 210. If the answer is negative (No) in step 501a (or when all the spots are not being irradiated), the central control unit 100 determines, on the basis of the irradiation interrupt-enabled flags shown in FIG. 5, whether or not the irradiation of the certain spot group can be interrupted in step 501. If the answer is affirmative (Yes) in step 501a (or when the irradiation is being performed), the central control unit 100 does not perform a subsequent irradiation interruption process until the central control unit 100 determines that all the spots are not being irradiated in step 501a.

If the answer is negative (No) in step 501 (or when the irradiation of the certain spot group cannot be interrupted), the central control unit 100 does not perform the subsequent irradiation interruption process until the Central control unit 100 determines that the irradiation of the certain spot group can be interrupted, and the process proceeds to step 213. In step 213, the scanning controller 41 adds 1 to the spot number (or the point to be irradiated is changed to the next spot). If the answer is affirmative (Yes) in step 501 (or when the irradiation of the spot, which can be interrupted, is completed, or when all the spots included in the group are irradiated), the central control unit 100 outputs the beam extraction stop command to the accelerator controller 40 and outputs the beam irradiation stop command to the scanning controller 41 in step 502.

The scanning controller 41 receives the beam irradiation stop command and interrupts a process of irradiating the subsequent j-th spot in step 503 (after step 210 is performed).

The accelerator controller 41 stops the extraction of the beam from the synchrotron 12 in step 504. After that, the accelerator controller 41 outputs a remaining beam deceleration command to the synchrotron 12 in step 505 and decelerates the beam that remains in the synchrotron 12.

When an event that causes irradiation to be interrupted occurs during the irradiation of a certain group that includes a certain spot (point to be irradiated), the central control unit 100 (second control unit) continuously controls the scanning controller 41 (first control unit) until the dose of the beam with which all spots that belong to the certain group are irradiated reaches a target dose in step 501. The central control unit 100 interrupts the control of the scanning controller 41 and causes the accelerator controller 40 to stop the extraction of the charged particle beam from the synchrotron 12 (accelerator) through steps 501 to 504.

The central control unit 100 determines whether or not the irradiation interruption cause is eliminated and the irradiation can be restarted in step 506. If the answer is affirmative (Yes) in step 506, the accelerator controller 40 outputs a beam acceleration command to the synchrotron 12 in step 507. Then, the accelerator controller 40 controls each magnet power supply so that each magnet is excited by a current with a set predetermined amount again. In addition, the accelerator controller 40 controls the radiofrequency power supply that applies radiofrequency power to the radiofrequency acceleration cavity so that the radiofrequency power and the frequency are increased to the predetermined values.

Simultaneously with the aforementioned control, the acceleration controller 40 outputs a recovery command to the scanning controller 41. When the scanning controller 41 receives the recovery command, the scanning controller 41 restarts the interrupted irradiation process on the j-th spot in step 508. However, since the dose of the beam with which the j-th spot is irradiated reaches the target dose (in step 209) in the system according to the present embodiment, the irradiation process on the j-th spot is immediately terminated. The scanning controller 41 determines whether or not the spot is the last spot in the layer in step 212. If the answer is negative (No) in step 212, the scanning controller 41 adds 1 to the spot number (or the point to be irradiated is changed to the next spot) in step 213. Then, the scanning controller 41 performs steps 205 and 206. In steps 205 and 206, the scanning controller 41 controls the scanning magnets (charged particle beam scanning units) 5A and 5B included in the scanning irradiation unit 15 to cause the scanning magnets to change the spot (point to be irradiated) and restarts the extraction of the charged particle beam from the synchrotron 12 (accelerator) after the change of the spot. After that, each step is repeated in the same manner as the normal operations. Then, a series of the irradiation processes on the affected part of the patient 30 are ended.

When the extraction of the charged particle beam is stopped by the accelerator controller 40 through steps 502 and 504 and an event that causes the irradiation to be interrupted is eliminated after the stop of the extraction, the central control unit 100 (second control unit) recovers the control of the scanning controller 41 (first control unit) through steps 507 and 508. After the recovery, the scanning controller 41 immediately controls the scanning magnets 5A and 5B (charged particle beam scanning units) to cause the scanning magnets 5A and 5B to change the spot (point to be irradiated) and restarts the extraction of the charged particle beam from the synchrotron 12 (accelerator) after the change of the spot.

Figure 9:
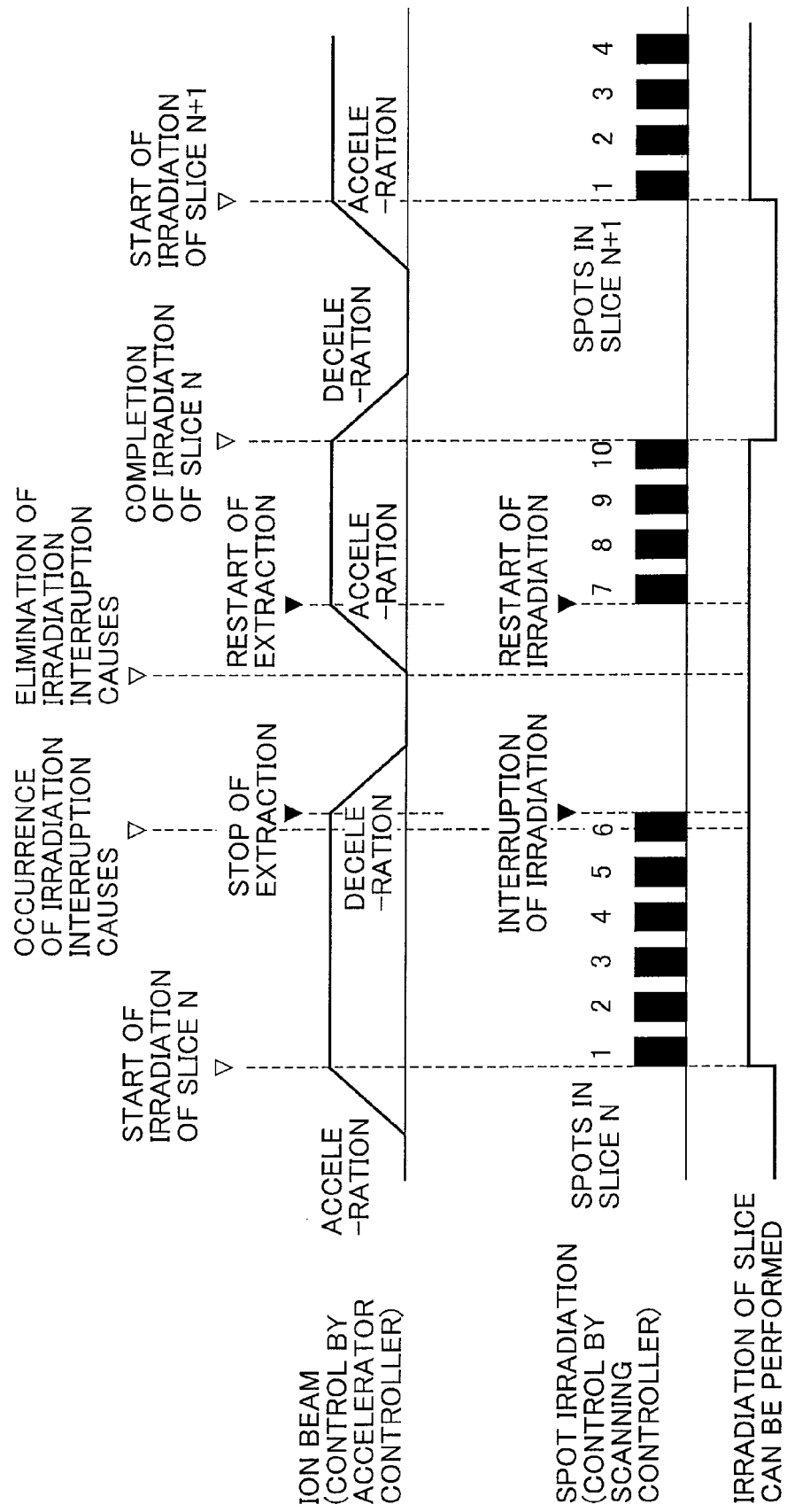
FIG. 9 is a timing chart showing an example of the relationship between a pattern of controlling an ion beam and spots irradiated with the ion beam in the conventional system.
Figure 10:
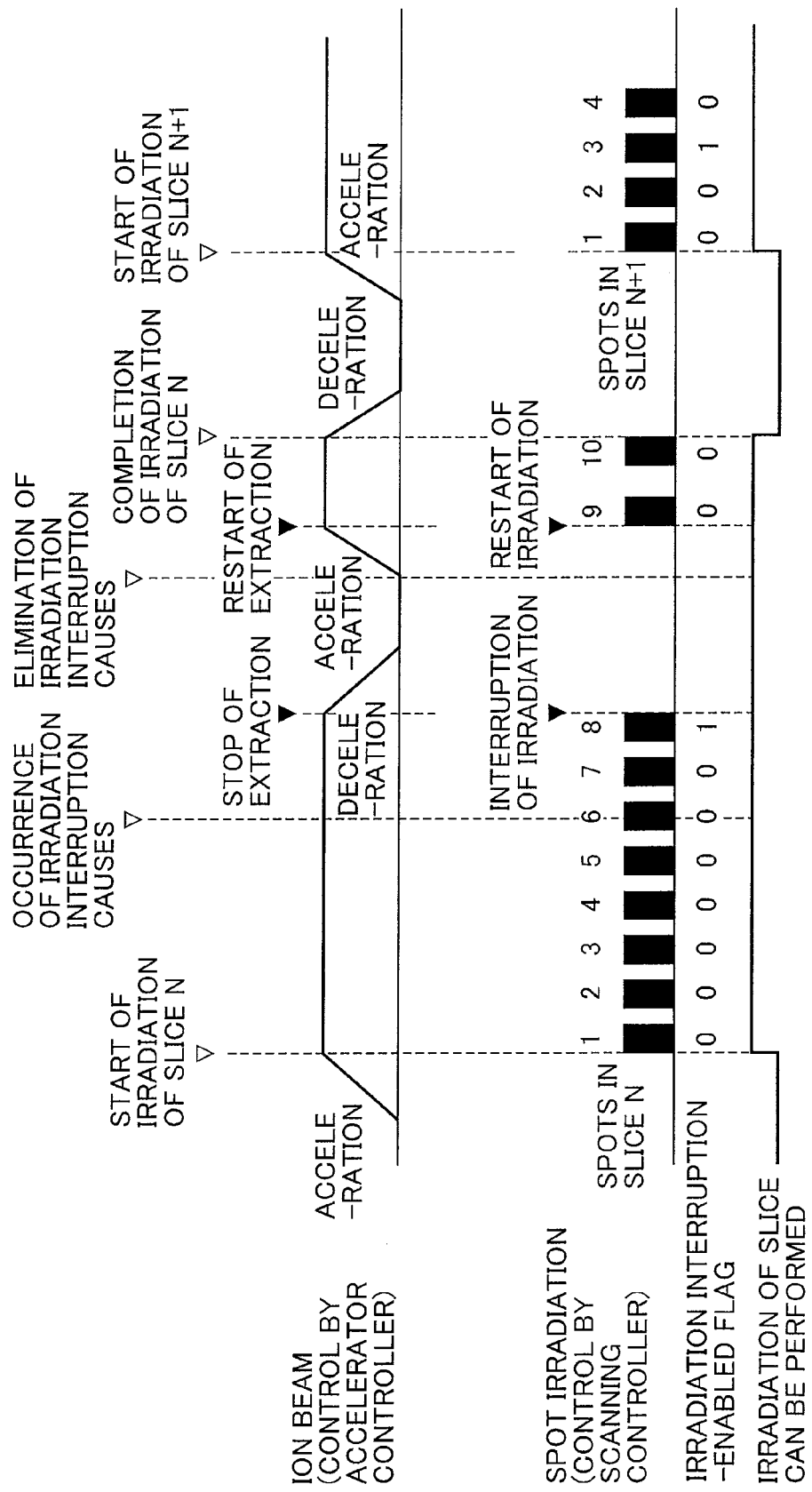
FIG. 10 is a timing chart showing an example of the relationship between a pattern of controlling an ion beam and spots irradiated with the ion beam in the embodiment of the present invention.

FIG. 9 shows an example of the relationship between a pattern of controlling the ion beam in the synchrotron 12 using energy and the irradiation of spots in the conventional system. FIG. 10 shows an example of the relationship between a pattern of controlling the ion beam in the synchrotron 12 using energy and the irradiation of spots in the system according to the present embodiment. In the conventional system, when an irradiation interruption cause occurs during irradiation of a spot, the extraction (irradiation) is stopped after completion of the irradiation of the spot, and an operation of decelerating the ion beam is immediately performed. In the present embodiment, when an irradiation interruption cause occurs during irradiation of a spot, the extraction (irradiation) is stopped when the irradiation of the whole spot group that includes the spot is completed, and an operation of decelerating the ion beam is performed.

In the process that is performed when an irradiation interruption cause occurs, the central control unit 100 performs the determination processes (using the control flags shown in FIG. 5 to determine whether or not irradiation of a spot group can be interrupted) shown in FIG. 8. In addition, the central control unit 100, the accelerator controller 40, and the scanning controller 41 cooperate with each other so that when an irradiation interruption cause occurs during the irradiation of a certain spot, the extraction (irradiation with the beam) of the beam is stopped after completion of the irradiation of a spot group that includes the certain spot without immediately stopping the extraction of the beam in the system using the scanning method. Thus, the irradiation is not stopped during the irradiation of the certain spot.

The present embodiment describes the process that is performed when an event that causes interruption of the irradiation occurs in the charged particle therapy system. When an event that causes the irradiation to be stopped occurs, the extraction (irradiation) is stopped and the series of irradiation processes are stopped in a similar manner to the conventional system from the perspective of safety.

The charged particle irradiation system configured in the aforementioned manner according to the present embodiment has the following effects.

In general, an irradiation dose distribution is evaluated with respect to the dose of a beam with which a group of spots is irradiated, not with respect to the dose of a beam with which only a spot is irradiated. If irradiation is interrupted due to a certain irradiation interruption cause during the irradiation of a certain spot included in a spot group, the irradiation interruption cause is eliminated, and the irradiation restarts to irradiate the certain spot, the spot may be misaligned and the dose distribution may be inappropriate due to misalignment of a device included in the system and misalignment of a patient.

Figure 11A:
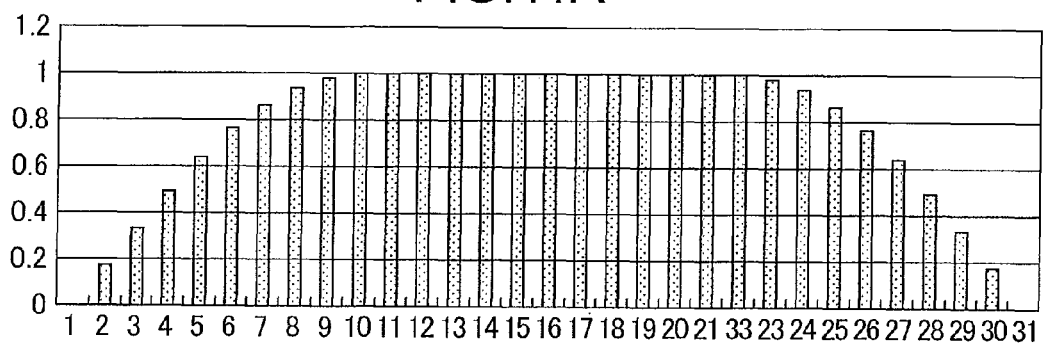
FIGS. 11A to 11C are diagrams showing an effect on a dose distribution when irradiation of a certain spot group is interrupted before completion of the irradiation and restarted.
Figure 11B:
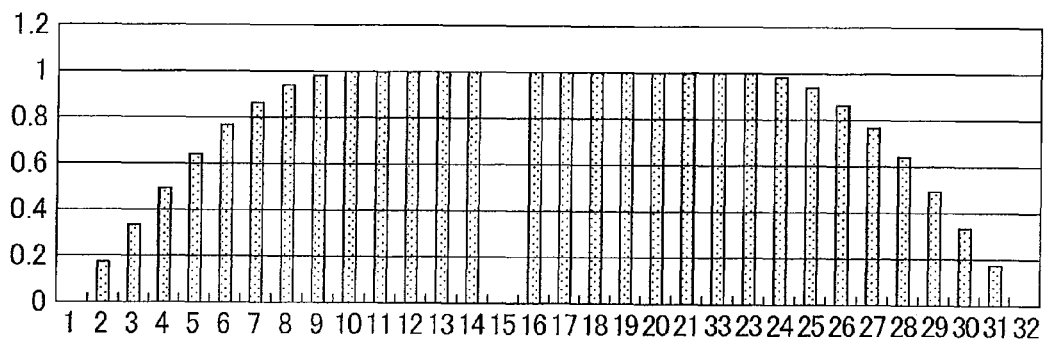
Figure 11C:
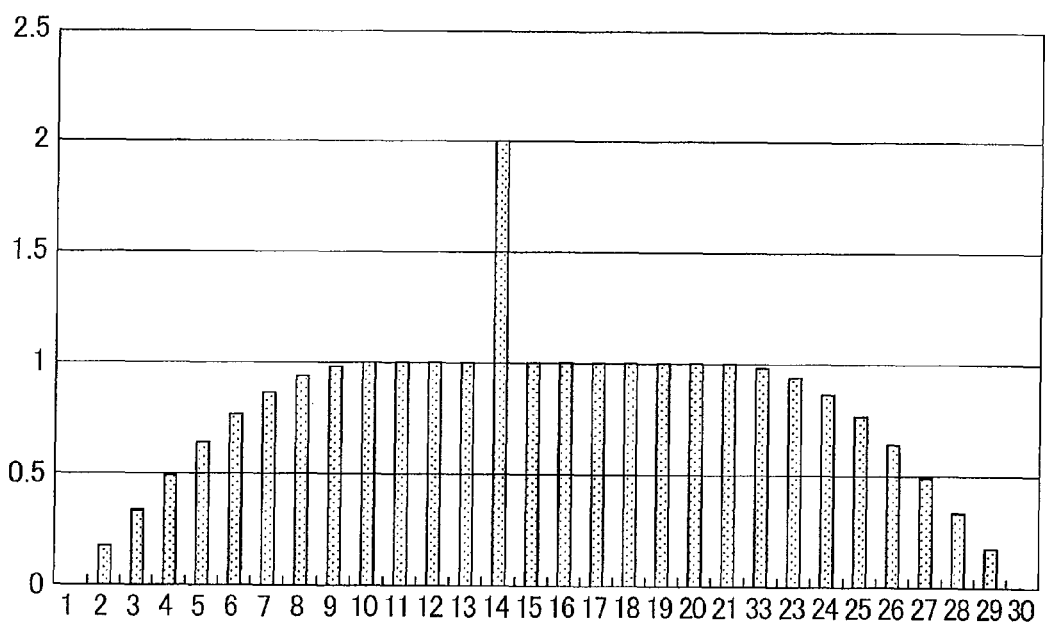

FIGS. 11A to 11C show effects on the dose distribution due to misalignment of spots in the case where irradiation is interrupted during the irradiation of a certain group of spots and restarts. For example, it is assumed that a dose distribution of the beam with which a group of spots Nos. 2 to 30 is irradiated needs to be obtained as shown in FIG. 11A. In the assumption, when the irradiation is interrupted during irradiation of a certain spot included in the group (after completion of irradiation of the spot No. 14) and the spot irradiation restarts with the spots Nos. 15 skipped (shifted one spot forward) due to positional misalignment, the spot No. 15 is not irradiated and a spot No. 31 is erroneously irradiated as shown in FIG. 11B. On the other hand, when the spot irradiation restarts with the spots Nos. 15 to 30 shifted one spot backward due to positional misalignment, the spot No. 14 is irradiated twice and the spot No. 30 is not irradiated as shown in FIG. 11C.

In the present embodiment, on the other hand, when an irradiation interruption cause (relatively minor failure in which continuous irradiation would be possible) occurs during the irradiation of a certain spot (spot No. 14), the irradiation is performed on a certain group of spots (spots Nos. 2 to 30) that include the certain spot without stopping the irradiation after completion of the irradiation of the certain spot. As a result, the planned dose distribution shown in FIG. 11A can be obtained in the present embodiment. When spots are preferably managed as a spot group, irradiation is not interrupted on a spot basis and is interrupted on a spot group basis. Therefore, the dose distribution is appropriate and the irradiation can be performed with high accuracy.

First to third examples of a spot group, which are suitable for the present embodiment, are described below. It is important how a spot group is defined beforehand in the present embodiment.

Figure 12A:
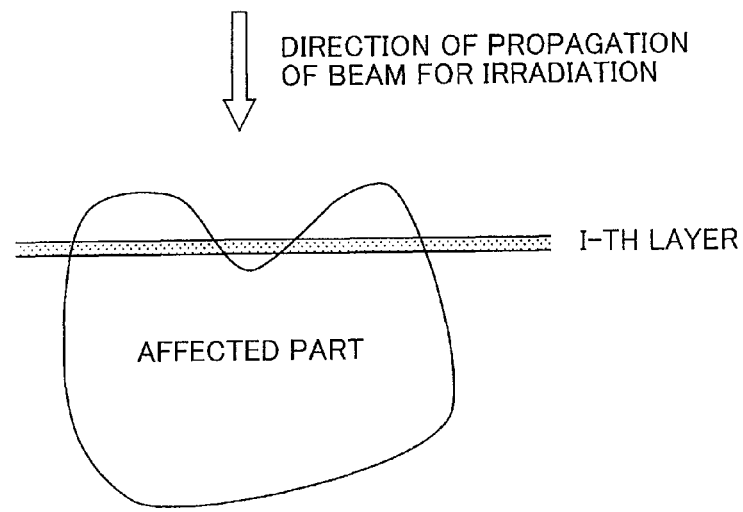
FIGS. 12A to 12C are diagrams showing spot groups in a first example.
Figure 12B:
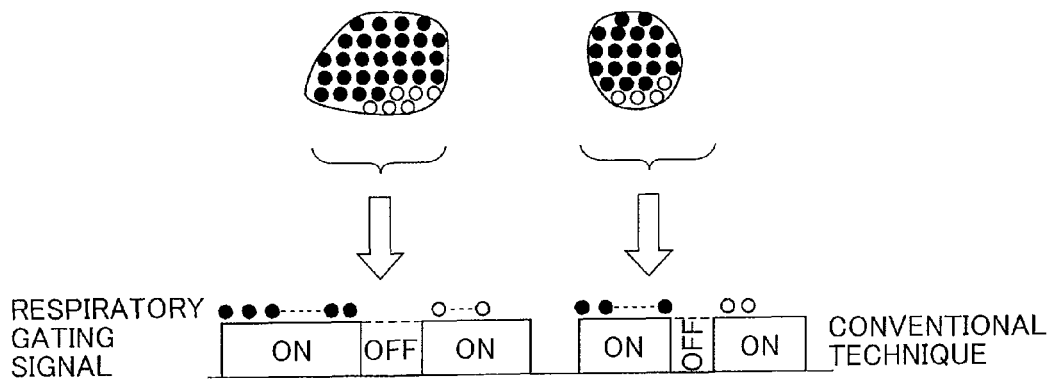
Figure 12C:
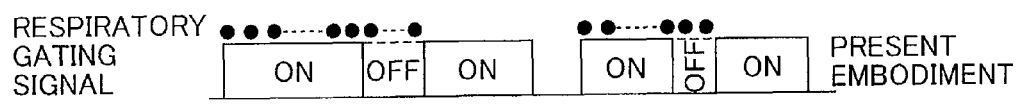

The first example describes the case where groups of spots are separated with each other in a single layer of the affected part. FIGS. 12A to 12C show the groups of spots in the first example. As shown in FIG. 12A, the affected part is separated into portions in the single layer depending on the shape of the affected part. In this case, it is preferable that the portions of the affected part be managed as spot groups.

In addition to the occurrence of a failure, a gating signal for respiratory gating is turned off as an irradiation interruption cause in some cases. In the respiratory gating, when the gating signal is turned on according to a respiratory phase, irradiation is performed. When the gating signal is turned off, the irradiation is stopped. Thus, the respiratory gating prevents a spot from being misaligned due to respiration, and irradiation can be stably performed.

However, an irradiation dose distribution is evaluated with respect to the dose of a beam with which a group of spots is irradiated, not with respect to the dose of a beam with which only a spot is irradiated. The respiratory gating may be performed on a priority basis. When the gating signal is turned off, the irradiation is interrupted. When the irradiation restarts after the interruption of the irradiation, the spots may be misaligned and the dose distribution may be inappropriate.

FIG. 12B is a diagram showing an operation that restarts after the irradiation is interrupted when the gating signal is turned off. Black circles indicate spots irradiated when the gating signal is turned on. White circles indicate spots irradiated in the case where the irradiation is interrupted when the gating signal is turned off and the irradiation restarts when the gating signal is turned on. The irradiation is forcibly performed on the single group of spots twice separately. As a result, the spots that are irradiated after the restart may be misaligned. Thus, the dose distribution may be inappropriate.

FIG. 12C is a diagram showing an operation according to the present embodiment. In the present embodiment, when spots are preferably managed as a spot group, irradiation of all the spots that are included in the group and are to be irradiated is performed on a priority basis. Even when the gating signal is turned off, the irradiation is continuously performed.

Since the irradiation is interrupted on a spot group basis, an appropriate irradiation dose distribution can be obtained and irradiation can be performed with high accuracy. In the present embodiment, the respiratory gating is preferably used for the spot irradiation.

In the second example, the number of spots that can be irradiated with one spill is calculated, and the spots are managed as a spot group. The number to be calculated is a unit of spots that can be irradiated with the beam that corresponds to one pulse of a pulse operation of the synchrotron 12. The treatment plan unit 140 calculates a target irradiation dose of the beam with which each spot is irradiated. In addition, the treatment plan unit 140 calculates the number of spots that can be irradiated with one spill. The calculated number of spots is managed as one unit. When the system is surely safe and a failure is surely minor, the irradiation is continuously performed on the spot group.

When the respiratory gating is applied, the treatment plan unit 140 may calculate the number of spots that can be irradiated when the gating signal is turned on, and the calculated number of spots may be managed as one unit.

In the third example, groups of spots overlap each other. In the charged particle irradiation system that uses the scanning method and is described in Japanese Patent No. 3681744, points to be irradiated are classified into some groups of spots (points to be irradiated), and the number of times of fractionated irradiation and the dose of a beam for one time of irradiation are preset. The irradiation is performed on a single spot multiple times separately so that the irradiation dose (irradiation time) for one time of irradiation of each spot is reduced and a variation in the irradiation dose for one time of irradiation of each spot is suppressed in the charged particle irradiation system. Thus, the actual irradiation dose can be reliably detected, and the dose distribution and the like can be reliably evaluated in the charged particle irradiation system.

However, since the charged particle irradiation system described in Japanese Patent No. 3681744 irradiates each of all spots multiple times, the treatment is prolonged and the efficiency of the system operation is low.

Figure 13A:
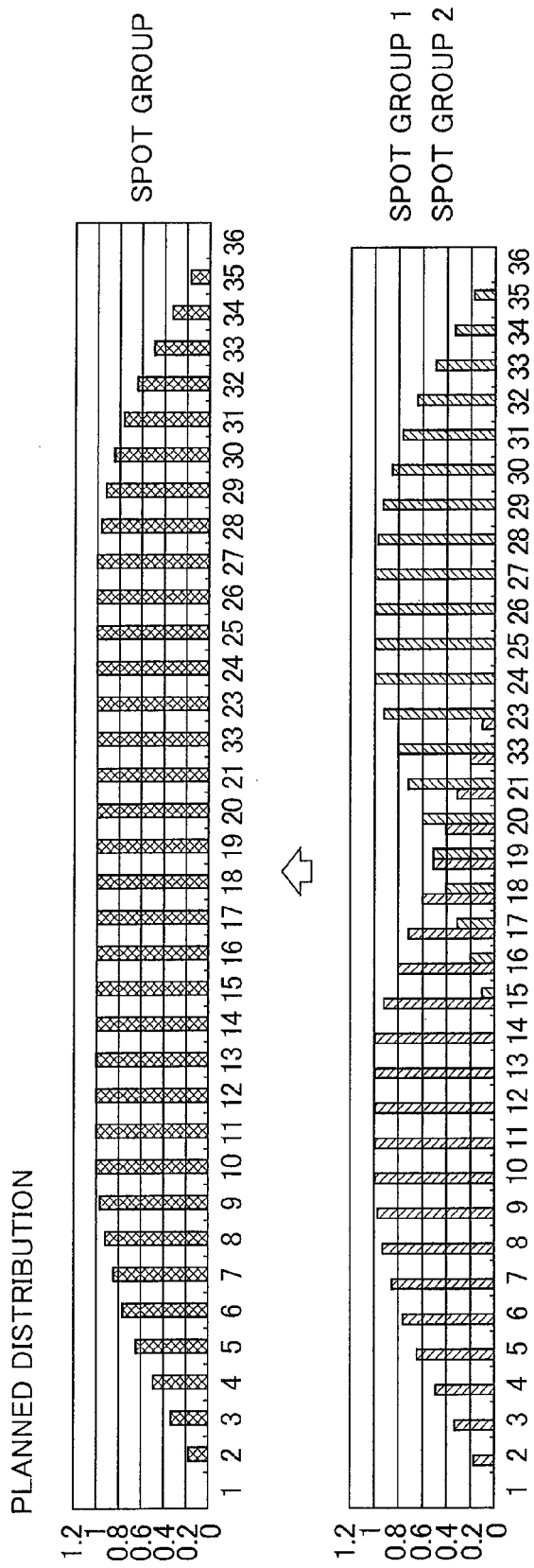
FIGS. 13A to 13C are diagrams showing spot groups in a third example.
Figure 13B:
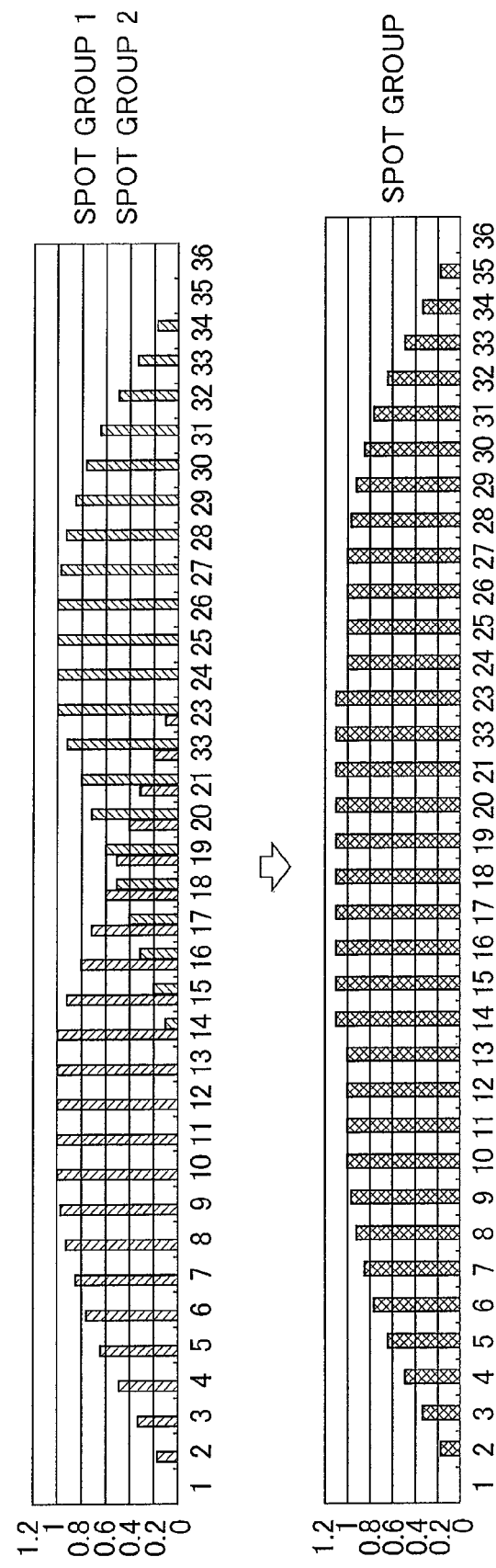
Figure 13C:
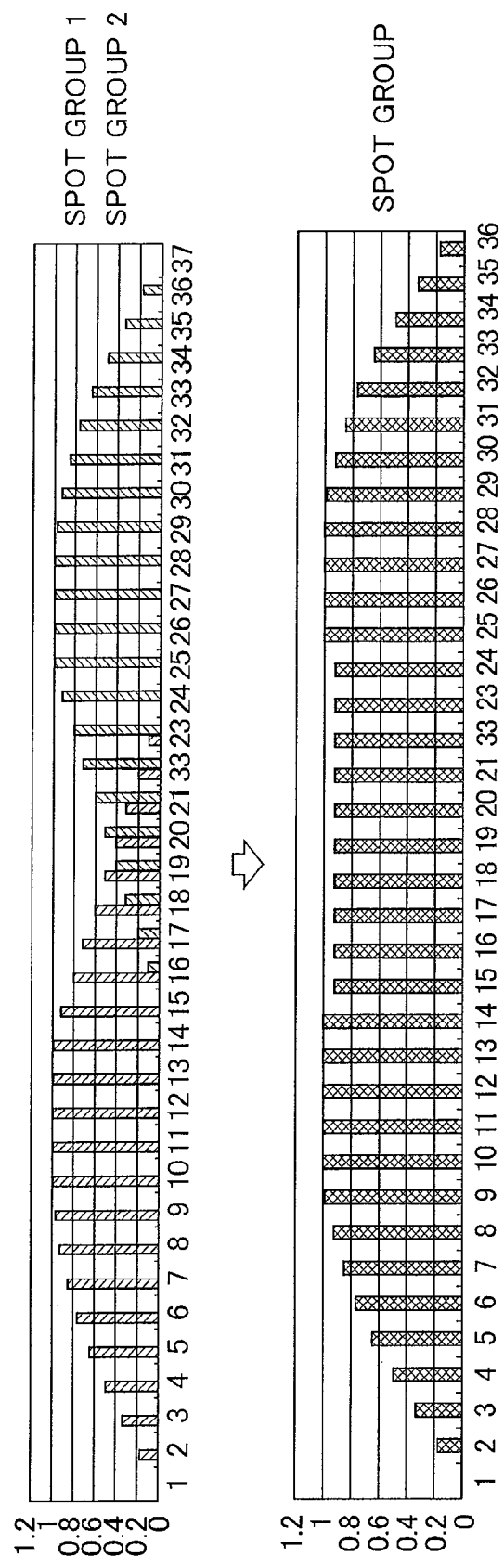

To avoid the aforementioned problems, an irradiation method in which spot groups overlap each other is proposed. FIGS. 13A to 13C are diagrams showing spot groups according to the third example.

As shown in the upper diagram of FIG. 13A, a distribution of the doses of beams with which spots Nos. 2 to 35 are irradiated is planned, for example. In this case, the spots Nos. 2 to 23 are managed as a first spot group, and the spots Nos. 15 to 35 are managed as a second spot group. For the first spot group, the dose is monotonically increased from the spot No. 2 to the spot No. 9. The doses of the beams with which the spots Nos. 9 to 14 are irradiated are the same. The dose is monotonically reduced from the spot No. 14 to the spot No. 23. The system is set so that the dose distribution for the first spot group is formed in a trapezoidal shape. For the second spot group, the dose is monotonically increased from the spot No. 15 to the spot No. 24. The doses of the beams with which the spots Nos. 24 to 28 are irradiated are the same. The dose is monotonically reduced from the spot No. 28 to the spot No. 35. The system is set so that the dose distribution for the second spot group is formed in a trapezoidal shape. For the first and second spot groups, the spots Nos. 15 to 23 overlap each other. Specifically, irradiation is performed on the first and second spot groups so that the dose distributions are formed as shown in the lower diagram of FIG. 13A. As a result, the dose distribution shown in the upper diagram of FIG. 13A can be obtained.

In the present embodiment, irradiation is not performed multiple times on each of all spots. Irradiation is performed on each spot while each of the first and second spot groups is managed as one unit. Thus, the treatment time can be reduced and the efficiency of the system operation can be increased.

Effects obtained when the present embodiment is applied to the third example are described below. In the present embodiment, each of the first and second spot groups is managed as one unit, and the irradiation of all the spots that are included in the groups and are to be irradiated is completed on a priority basis. Even when a relatively minor failure occurs during the irradiation of the first spot group, the irradiation is continuously performed on the first spot group. After the irradiation of the first spot group (spots Nos. 2 to 23) is completed, the irradiation is stopped. When the irradiation interruption event is eliminated, the first spot of the second spot group (Nos. 15 to 35) is irradiated. Even when a relatively minor failure occurs during the irradiation of the second spot group, the irradiation is continuously performed on the second spot group.

The upper diagram of FIG. 13B shows the case where the spots irradiated after the interruption of the irradiation are shifted one spot backward. The lower diagram of FIG. 13B shows the effect of the present embodiment. In the example shown in FIG. 13B, the first spot group (spots Nos. 2 to 23) is irradiated as planned, but the spots (Nos. 15 to 35) of the second spot group are shifted one spot backward. Thus, the spots of the second spot group are irradiated and positioned at spots Nos. 14 to 34. However, when the combination of the first and second spot groups is evaluated, the dose distribution is formed as shown in the lower diagram of FIG. 13B. In comparison with the planned dose distribution shown in the upper diagram of FIG. 13A, the spot No. 35 is not irradiated, and the spots Nos. 14 to 23 are irradiated with a slightly large dose of beams in the example shown in FIG. 13B. Thus, the shifted spots less affect the dose distribution shown in FIG. 13B.

The upper diagram of FIG. 13C shows the case where the spots irradiated after the interruption of the irradiation are shifted one spot forward. The lower diagram of FIG. 13C shows the effect of the present embodiment. In the example shown in FIG. 13C, the first spot group (spots Nos. 2 to 23) is irradiated as planned, but the spots (Nos. 15 to 35) of the second spot group are shifted one spot forward. Thus, the spots of the second spot group are irradiated and positioned at spots Nos. 16 to 36. However, when the combination of the first and second spot groups is evaluated, the dose distribution is formed as shown in the lower diagram of FIG. 13C. In comparison with the planned dose distribution shown in the upper diagram of FIG. 13A, the spot No. 36 is erroneously irradiated, and the spots Nos. 15 to 24 are irradiated with a slightly small dose of beams in the example shown in FIG. 13C. Thus, the shifted spots less affect the dose distribution shown in FIG. 13C.

Therefore, the efficiency of the system operation is improved, and the irradiation is interrupted on a spot group basis. Thus, the dose distribution is appropriately formed and the irradiation can be performed with high accuracy. In the present embodiment, the irradiation method described in the third example is preferably used.

In the present embodiment, even when a failure occurs, the irradiation is continuously performed depending on the type and level of the cause of the failure. From the perspective of safety of the patient and the operator, it is very important to specify the type or level of a cause in which continuous irradiation would be possible.

The irradiation with the ion beam, which is performed while the spot scanning is performed, can be applied to a proton beam irradiation system that uses a cyclotron as an accelerator.

What is claimed is:

1. A charged particle irradiation system comprising:
   an accelerator from which a charged particle beam is extracted;
   an irradiation unit that has a charged particle beam scanning unit and irradiates an irradiation spot with the charged particle beam extracted from the accelerator; and
   a control unit configured to, when an event that causes the irradiation to be interrupted occurs during the irradiation of the irradiation spot with the charged particle beam, continue the extraction of the charged particle beam from the accelerator until the irradiation of all spots of a spot group including a plurality of spots reach target doses; and
   stop the extraction of the charged particle beam from the accelerator at the time of completion of the irradiation of all spots that belong to the spot group,
   wherein, the spot group is predefined and includes a plurality of spots, including the irradiation spot.

2. The charged particle irradiation system according to claim 1,
   wherein when the event that causes the irradiation to be interrupted is eliminated after stopping the extraction of the charged particle beam, the control unit immediately changes the irradiation spot and restarts the extraction of the charged particle beam from the accelerator so that irradiation is performed from a first spot of a next spot group.

3. The charged particle irradiation system according to claim 1,
   wherein said spot group includes a first spot group and a second spot group that are predefined such that the first and second spot groups comprise overlapping spots belonging to both of the first and second spot groups, and
   said control unit stops the extraction of the charged particle beam from the accelerator at the time of completion of the irradiation of all spots that belong to the first spot group even when said event occurs.

4. A charged particle irradiation system comprising:
   an accelerator from which a charged particle beam is extracted;
   an irradiation unit that has a charged particle beam scanning unit and irradiates, with the charged particle beam extracted from the accelerator, an irradiation spot that is a spot to be irradiated;
   a first control unit configured to stop the extraction of the charged particle beam from the accelerator when a dose of the charged particle beam with which the irradiation spot is irradiated reaches a target dose,
   control the charged particle beam scanning unit to cause the charged particle beam scanning unit to change the irradiation spot a next irradiation spot, that is a spot to be irradiated next to the irradiation spot, under the condition that the extraction of the charged particle beam is stopped,
   and restart the extraction of the charged particle beam from the accelerator after the charged particle beam scanning unit changes the irradiation spot to the next irradiation spot; and
   a second control unit configured to, when an event that causes the irradiation to be interrupted occurs during the irradiation of the irradiation spot with the charged particle beam, continuously control the first control unit until the dose of the charged particle beam with which the irradiation spot is irradiated reaches the target dose,
   continuously control the first control unit in order to irradiate the next irradiation spot when the dose of the charged particle beam with which the irradiation spot is irradiated reaches the target dose, and
   interrupt the control of the first control unit and stop the extraction of the charged particle beam from the accelerator at the time of completion of the irradiation of all spots that belong to a spot group, such that even when said event occurs the irradiation is continued until all spots of the spot group reach target doses,
   wherein the spot group is predefined and includes a plurality of spots, including the irradiation spot, and the next irradiation spot.

5. The charged particle irradiation system according to claim 4,
wherein when the event that causes the irradiation to be interrupted is eliminated after the stop of the extraction of the charged particle beam, the second control unit causes the first control unit to recover the control that stops the extraction of the charged particle beam from the accelerator, controls the charged particle beam scanning unit and restarts the extraction of the charged particle beam from the accelerator, after the recovery of the control, the first control unit immediately controls the charged particle beam scanning unit so that the charged particle beam scanning unit changes the irradiation spot and restarts the extraction of the charged particle beam from the accelerator after the change of the irradiation spot so as to perform irradiation from a first spot of a next spot group.

6. The charged particle irradiation system according to claim 4,
wherein said spot group includes a first spot group and a second spot group that are predefined such that the first and second spot groups comprise overlapping spots belonging to both of the first and second spot groups, and said second control unit stops the extraction of the charged particle beam from the accelerator at the time of completion of the irradiation of all spots that belong to the first spot group even when said event occurs.

7. A method for controlling a charged particle irradiation system that includes an accelerator from which a charged particle beam is extracted, and an irradiation unit that has a charged particle beam scanning unit and irradiates an irradiation spot in a spot group that is predefined and includes a plurality of spots, including the irradiation spot, with the charged particle beam extracted from the accelerator, the method comprising the steps of:
when an event that causes the irradiation to be interrupted occurs during the irradiation of the irradiation spot with the charged particle beam, continuing the extraction of the charged particle beam from the accelerator until the irradiation of all spots of the spot group reach target doses,
stopping the extraction of the charged particle beam from the accelerator at the time of completion of irradiation of all spots that belong to the spot group.

8. The method according to claim 7, further comprising the steps of, when the event that causes the irradiation to be interrupted is eliminated after the stop of the extraction of the charged particle beam, immediately changing the irradiation spot and restarting the extraction of the charged particle beam from the accelerator so that irradiation is performed from a first spot of a next spot group.

9. A method for controlling a charged particle irradiation system that includes an accelerator from which a charged particle beam is extracted, and an irradiation unit that has a charged particle beam scanning unit and irradiates an irradiation spot in a spot group that is predefined and includes a plurality of spots, including an irradiation spot and a next irradiation spot, with the charged particle beam extracted from the accelerator, the method comprising:

a first step of stopping the extraction of the charged particle beam from the accelerator when a dose of the charged particle beam with which the irradiation spot is irradiated reaches a target dose, controlling the charged particle beam scanning unit to cause the charged particle beam scanning unit to change the irradiation spot to the next irradiation spot, that is a spot to be irradiated next to the irradiation spot, under the condition that the extraction of the charged particle beam is stopped, and restarting the extraction of the charged particle beam from the accelerator after the change of the irradiation spot to the next irradiation spot; and a second step of, when an event that causes the irradiation to be interrupted has occurred during the irradiation of the irradiation spot with the charged particle beam, continuously extracting the charged particle beam until the dose of the charged particle beam with which the irradiation spot is irradiated reaches the target dose, and controlling the charged particle beam scanning unit to cause the charged particle beam scanning unit to change the irradiation spot to the next irradiation spot, that is a spot to be irradiated next to the irradiation spot when the dose of the charged particle beam with which the irradiation spot is irradiated reaches the target dose; and a third step of continuously repeating the second step with the next irradiation spot as the irradiation spot until completing the irradiation of all spots that belong to the spot group and then interrupting the second step and stopping the extraction of the charged particle beam from the accelerator at the time of completion of the irradiation of all spots that belong to the spot group, such that even when said event occurs the irradiation is continued until all spots of the spot group reach target doses.

10. The method according to claim 9,
wherein the second step or third step restarts the first step when the event that causes the irradiation to be interrupted is eliminated after the stop of the extraction of the charged particle beam, and in the first step, the charged particle beam scanning unit is controlled immediately after the restart of the first step to change the irradiation spot to the next spot, and the extraction of the charged particle beam from the accelerator is restarted after the change of the irradiation spot so that irradiation is performed from a first spot of a next spot group.

* * * * *